(12) United States Patent
Kuo et al.

(10) Patent No.: US 6,194,902 B1
(45) Date of Patent: *Feb. 27, 2001

(54) PIPE TESTING APPARATUS AND METHOD USING ELECTRICAL OR ELECTROMAGNETIC PULSES TRANSMITTED INTO THE PIPE

(76) Inventors: John T. Kuo, 11 Hoffman La., Blauvelt, NY (US) 10913; Gale D. Burnett, 9191 Northwood Rd., Lynden, WA (US) 98264

(*) Notice: Subject to any disclaimer, the term of this patent is extended or adjusted under 35 U.S.C. 154(b) by 0 days.

This patent is subject to a terminal disclaimer.

(21) Appl. No.: 08/807,645

(22) Filed: Feb. 27, 1997

Related U.S. Application Data

(60) Provisional application No. 60/012,336, filed on Feb. 27, 1996.

(51) Int. Cl.[7] .......................... G01R 31/08; G01R 31/11; G01R 31/12
(52) U.S. Cl. .......................................... 324/637; 324/535
(58) Field of Search .................... 324/637, 639, 324/532, 535

(56) References Cited

U.S. PATENT DOCUMENTS

| | | |
|---|---|---|
| 1,745,419 | 2/1930 | Henneberger . |
| 2,124,579 | 7/1938 | Knerr et al. . |
| 2,522,362 | 9/1950 | Gilbert . |
| 2,570,912 | 10/1951 | Bishop . |
| 2,602,834 | 7/1952 | Leslie et al. . |
| 2,650,344 | 8/1953 | Lloyd . |
| 2,725,526 | 11/1955 | Stringfield et al. . |
| 2,731,598 | 11/1956 | Herbert . |
| 2,887,652 | 5/1959 | Bendayan et al. . |
| 2,935,728 | 5/1960 | Morgan . |
| 3,055,209 | 9/1962 | Reid et al. . |
| 3,264,864 | 8/1966 | Reid et al. . |
| 3,273,055 | 9/1966 | Quittner . |
| 3,400,363 | 9/1968 | Silverman . |
| 3,526,831 | 9/1970 | Smith . |
| 3,600,674 | 8/1971 | Roberts et al. . |
| 3,609,533 | 9/1971 | Pardis . |
| 3,670,240 | 6/1972 | Maranchak et al. . |
| 3,747,085 | 7/1973 | Bala et al. . |
| 3,757,287 | 9/1973 | Bealor, Jr. . |
| 3,909,712 | 9/1975 | Rietz . |
| 3,924,179 | 12/1975 | Dozier . |
| 3,991,364 | 11/1976 | Wiznerowicz . |

(List continued on next page.)

FOREIGN PATENT DOCUMENTS

| | | |
|---|---|---|
| 2210167 | 9/1973 | (DE) . |
| 3533479 | 3/1987 | (DE) . |
| WO890685 | 7/1989 | (WO) . |

*Primary Examiner*—Walter E. Snow
(74) *Attorney, Agent, or Firm*—Hughes & Schacht, PS; Robert B. Hughes

(57) ABSTRACT

A method and system for detecting corrosion on a pipe or a pipeline. An electrical or electromagnetic pulse is transmitted into a pipe or pipeline to travel as a propagating electromagnetic wave along the pipeline to a receiving location. Both the distance traveled from the transmitting and receiving location, and also the time interval for such travel are measured. Velocity of the wave is detected as a means of ascertaining whether corrosion is present. Various embodiments, using both multi-channel and single cables, are used to transmit the detected waves, and the waves are received at a plurality of spaced locations along the length of the pipe or pipeline. For an insulated pipeline, the signals can be received by a directional antenna, and the pulses can be transmitted into the pipeline by means of either an antenna placed directly adjacent to the pipeline or a magnet electrical contact member in direct contact with the pipeline.

67 Claims, 18 Drawing Sheets

U.S. PATENT DOCUMENTS

| | | |
|---|---|---|
| 3,992,923 | 11/1976 | Roberts . |
| 4,039,938 | 8/1977 | Link . |
| 4,063,161 | 12/1977 | Pardis . |
| 4,083,229 | 4/1978 | Anway . |
| 4,099,117 | 7/1978 | Erath . |
| 4,112,349 | 9/1978 | Weber . |
| 4,118,662 | 10/1978 | Weber . |
| 4,142,143 | 2/1979 | Daniel . |
| 4,172,382 | 10/1979 | Murphy et al. . |
| 4,255,710 | 3/1981 | Weber . |
| 4,289,019 | 9/1981 | Claytor . |
| 4,291,204 | 9/1981 | Crick . |
| 4,319,348 | 3/1982 | Suzuki . |
| 4,326,416 | 4/1982 | Fredberg . |
| 4,347,622 | 8/1982 | Bernatowicz et al. . |
| 4,389,593 | 6/1983 | DeSantis et al. . |
| 4,404,514 | 9/1983 | Reichert, Jr. . |
| 4,427,940 | 1/1984 | Hirama et al. . |
| 4,430,613 | 2/1984 | French . |
| 4,471,294 | 9/1984 | Nielsen . |
| 4,495,465 | 1/1985 | Tomaiuolo et al. . |
| 4,538,103 | 8/1985 | Cappon . |
| 4,591,785 | 5/1986 | Hoehn, Jr. . |
| 4,648,081 | 3/1987 | Burns . |
| 4,695,788 | 9/1987 | Marshall . |
| 4,739,276 | 4/1988 | Graube et al. . |
| 4,742,298 | 5/1988 | Ando et al. . |
| 4,755,742 | 7/1988 | Agoston et al. . |
| 4,769,598 | 9/1988 | Krieg et al. . |
| 4,829,284 | 5/1989 | Pfaff . |
| 4,839,593 | 6/1989 | Spies . |
| 4,843,319 | 6/1989 | Spies . |
| 4,843,320 | 6/1989 | Spies . |
| 4,855,565 | 8/1989 | Saitoh et al. . |
| 4,906,925 | 3/1990 | Kiminkinen . |
| 4,906,937 | 3/1990 | Wikstrom et al. . |
| 4,911,012 | 3/1990 | Ziska . |
| 4,929,896 | 5/1990 | Lara . |
| 4,929,898 | 5/1990 | Spies . |
| 4,929,903 | 5/1990 | Saigo et al. . |
| 4,970,467 | 11/1990 | Burnett . |
| 4,990,851 | 2/1991 | Spies . |
| 4,996,879 | 3/1991 | Kruka et al. . |
| 5,070,537 | 12/1991 | Ohira et al. . |
| 5,087,853 | 2/1992 | Murphy et al. . |
| 5,121,058 | 6/1992 | Allison et al. . |
| 5,126,654 | 6/1992 | Murphy et al. . |
| 5,189,374 | 2/1993 | Burnett . |
| 5,243,294 | 9/1993 | Burnett . |
| 5,254,944 | 10/1993 | Holmes et al. . |
| 5,270,661 | 12/1993 | Burnett . |
| 5,321,356 | 6/1994 | Weischedel . |
| 5,333,502 | 8/1994 | Clark, Jr. et al. . |
| 5,446,369 | 8/1995 | Byrne et al. . |
| 5,481,191 | 1/1996 | Patel . |
| 5,526,691 | 6/1996 | Latimer et al. . |
| 5,530,367 | 6/1996 | Bottman . |
| 5,581,037 | 12/1996 | Kwun et al. . |
| 5,635,645 | 6/1997 | Ottes et al. . |
| 5,719,503 | 2/1998 | Burnett . |

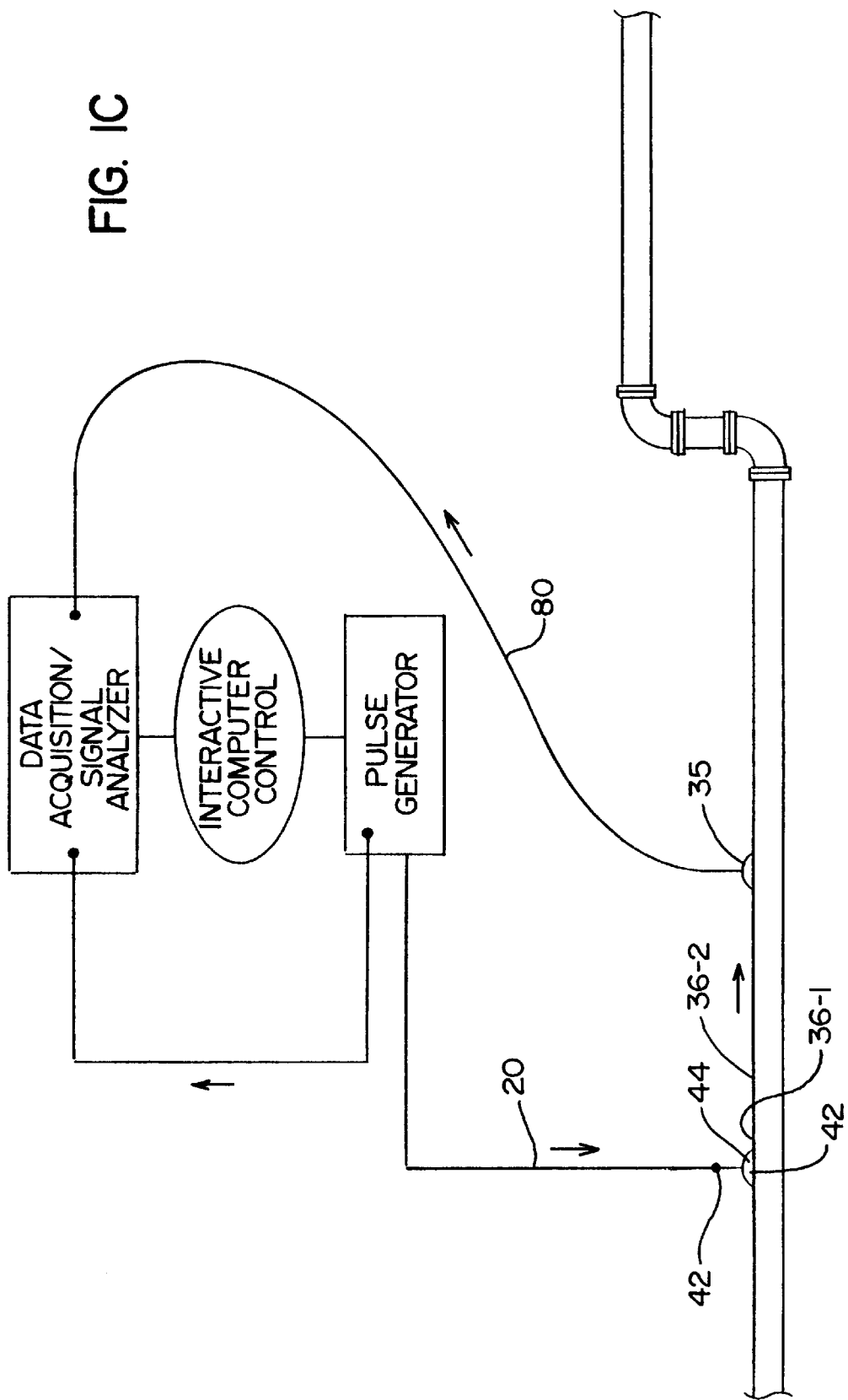

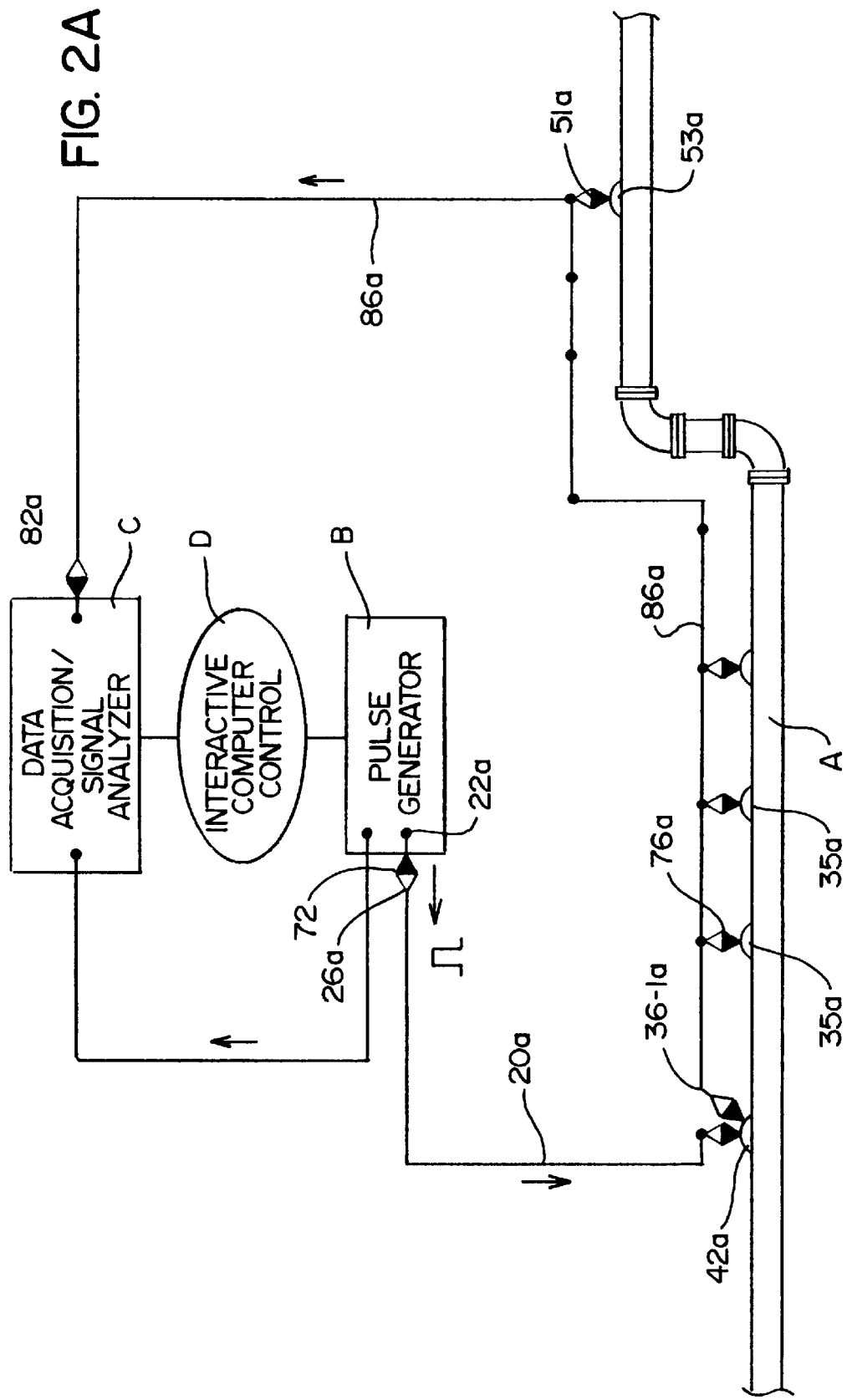

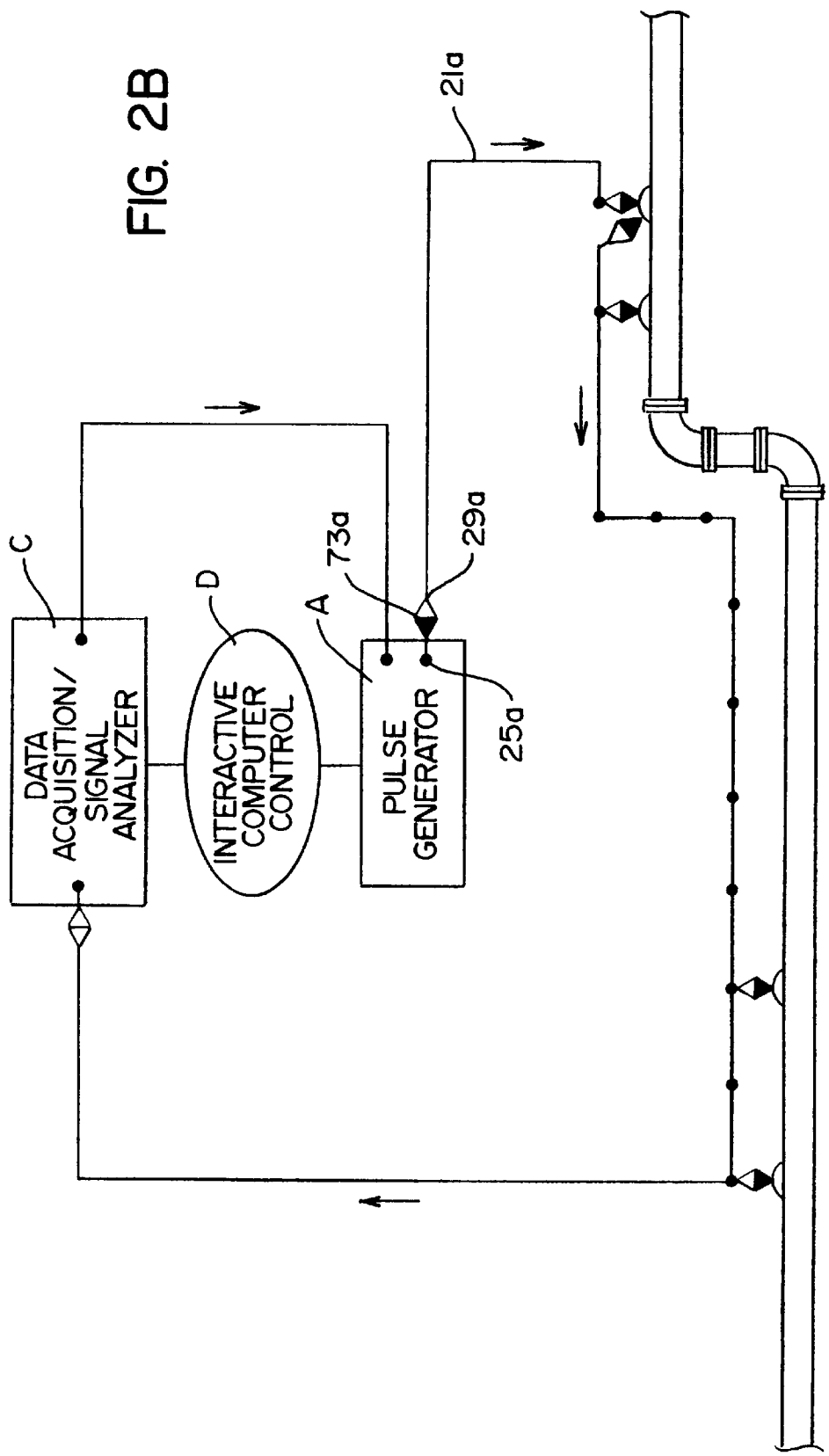

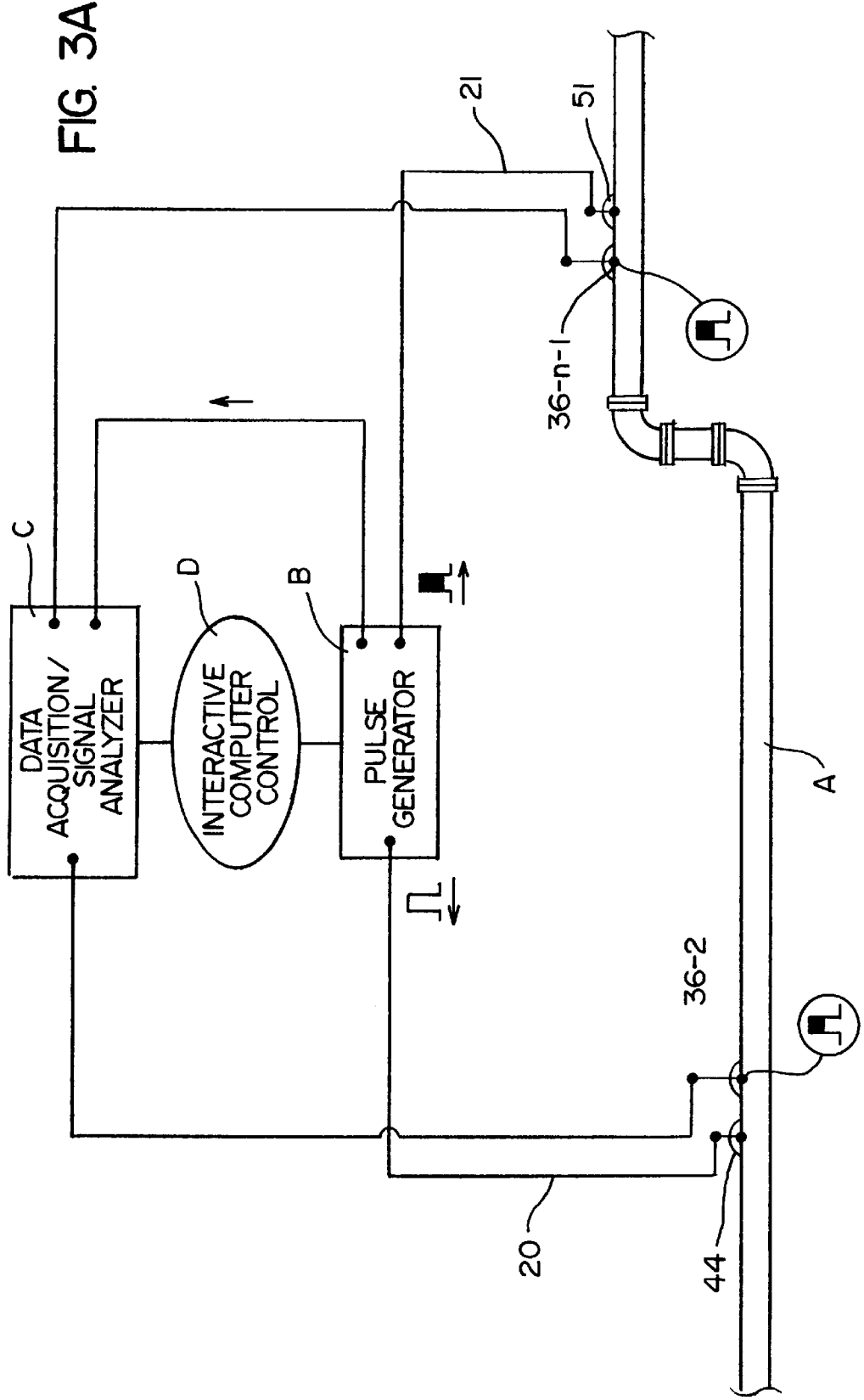

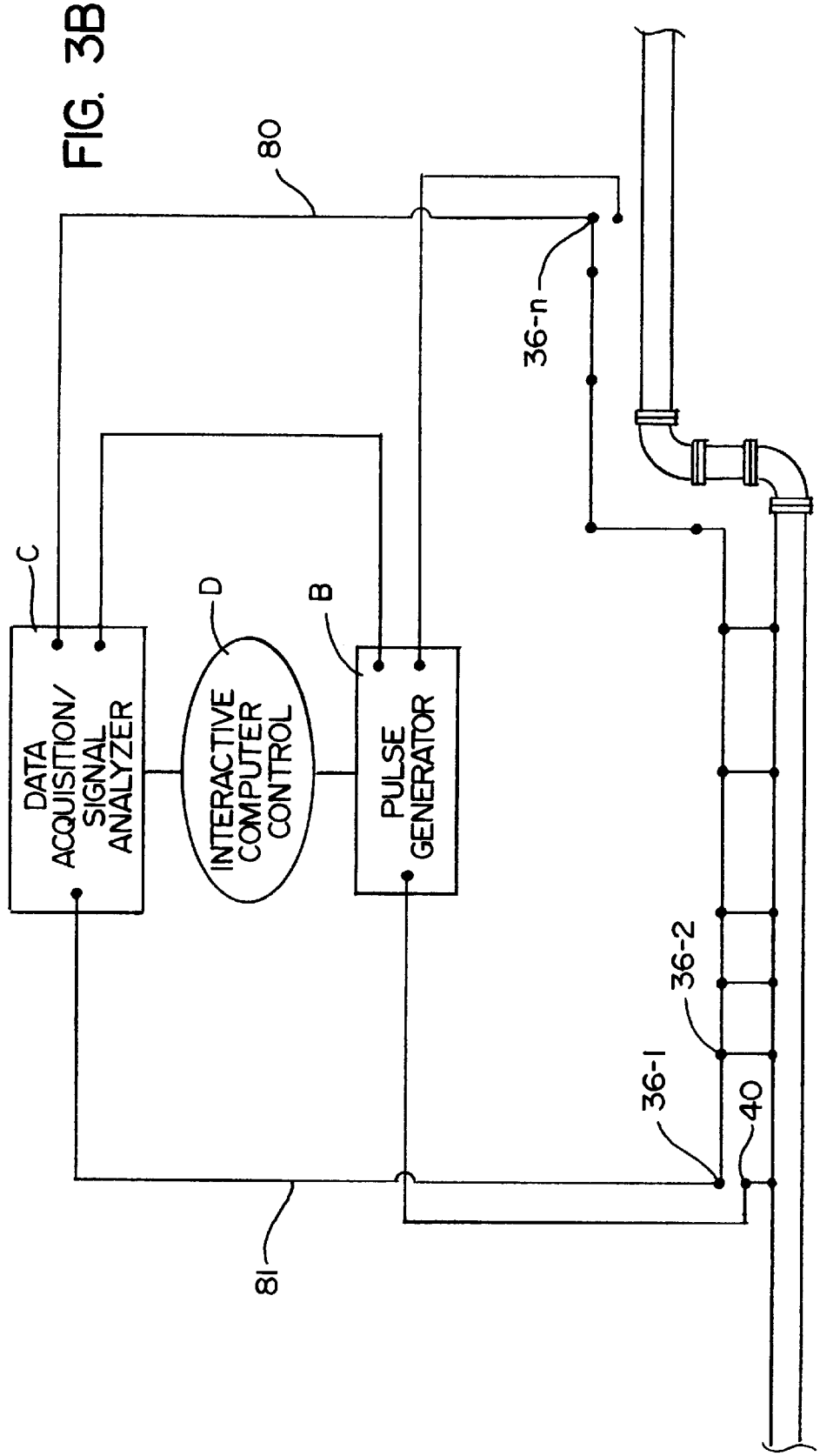

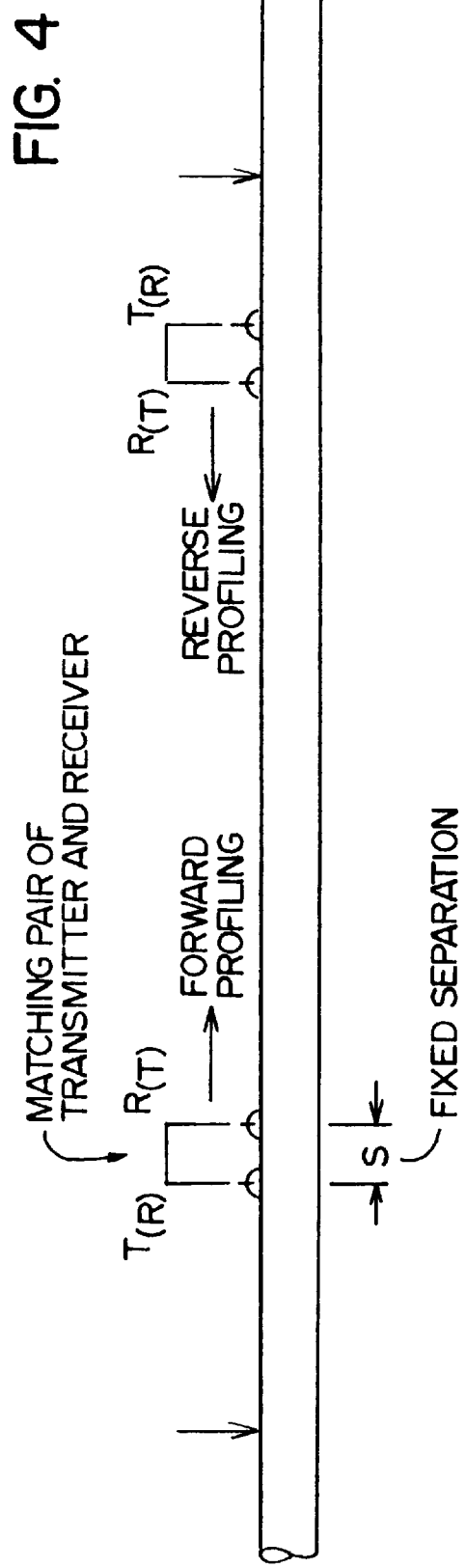

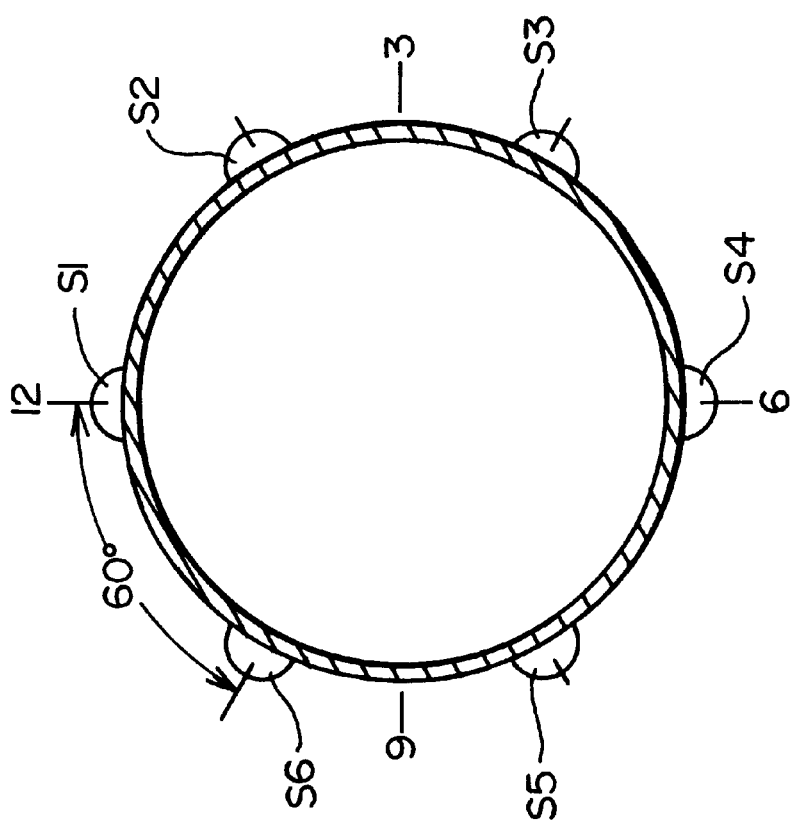
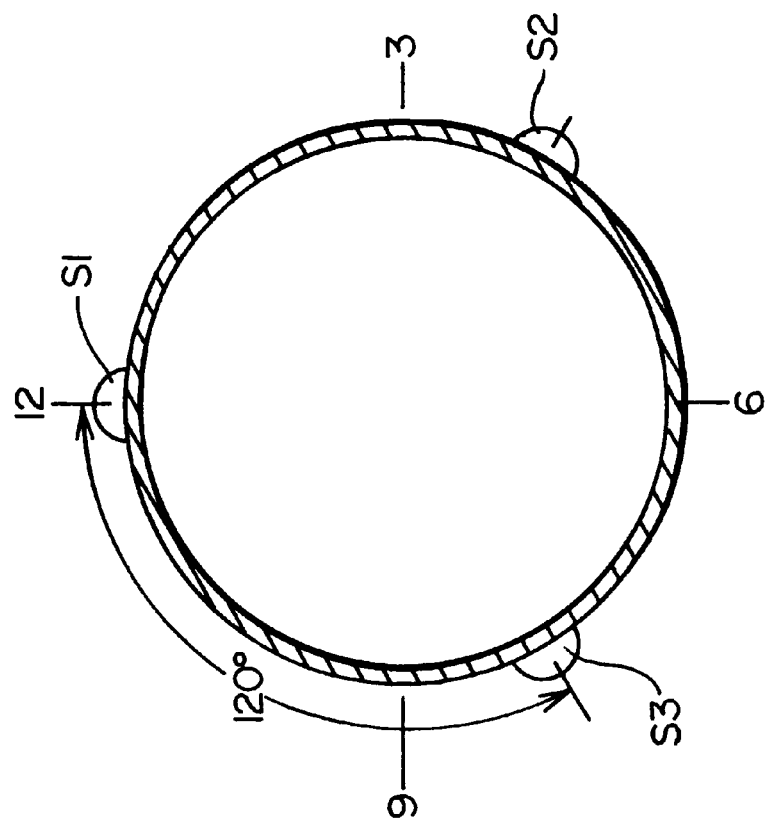

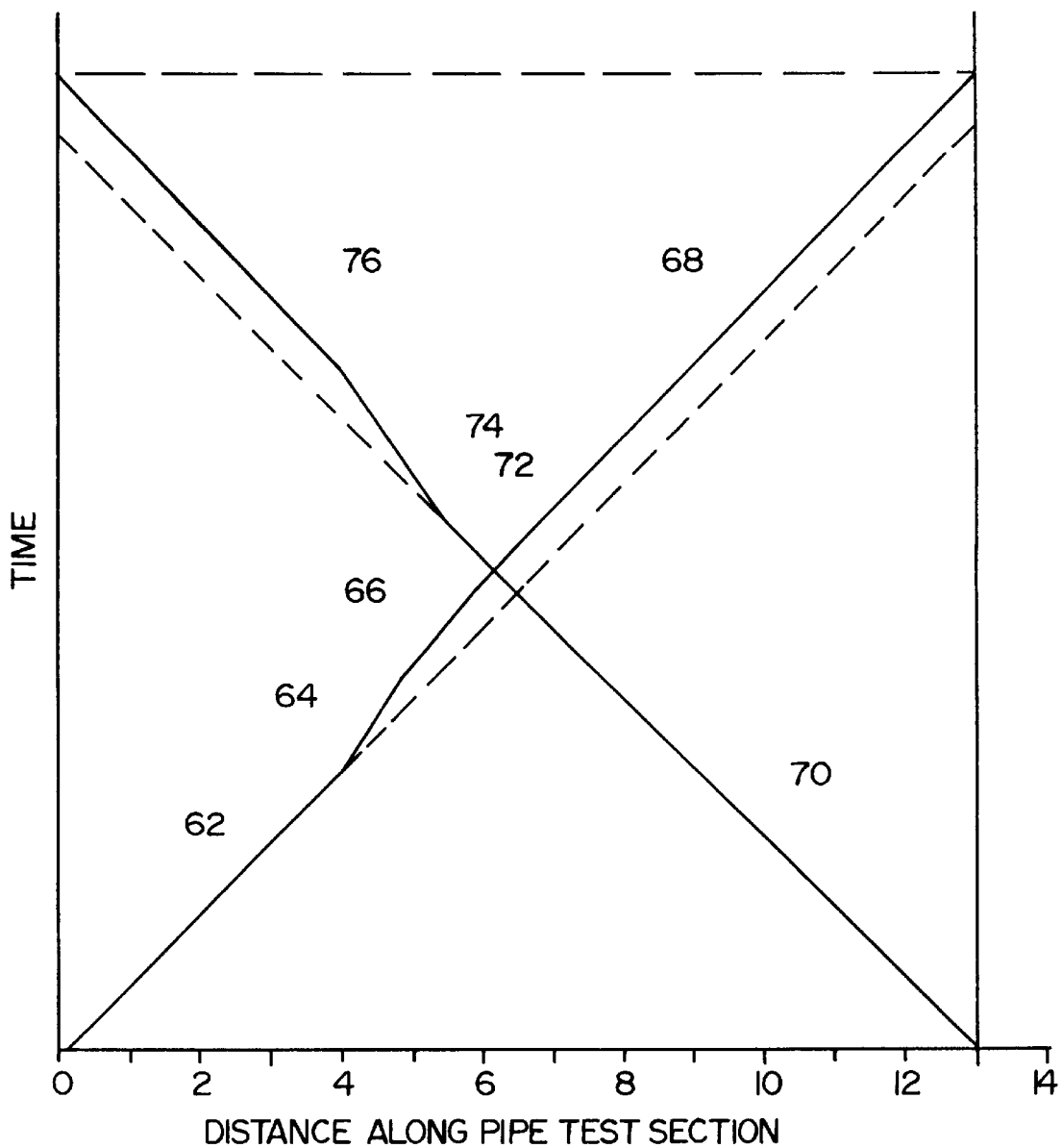

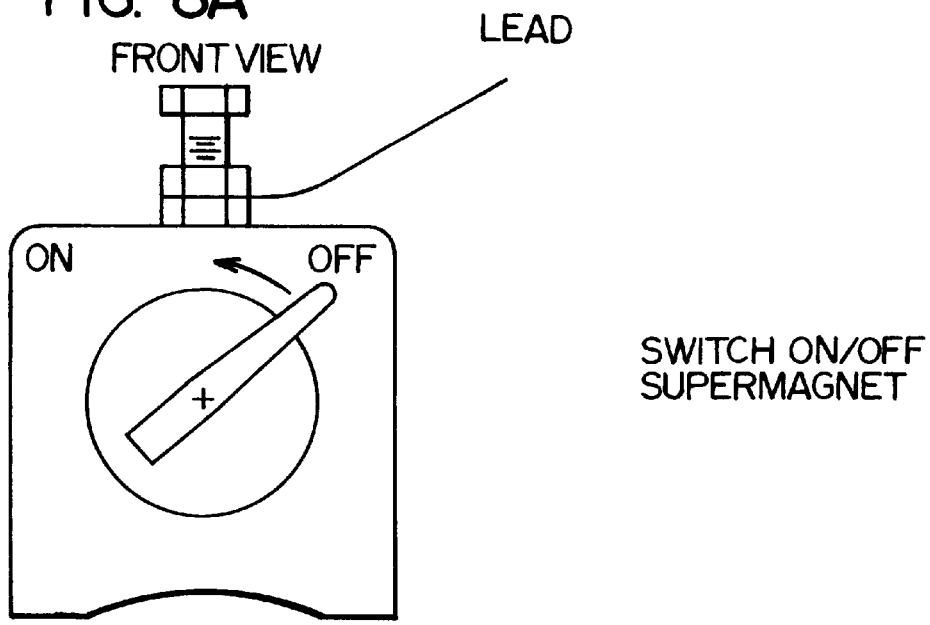
SWITCH ON/OFF
SUPERMAGNET
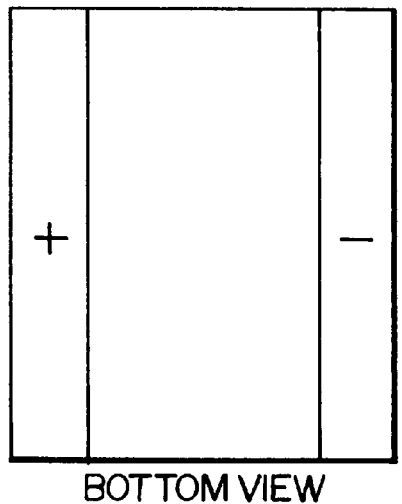
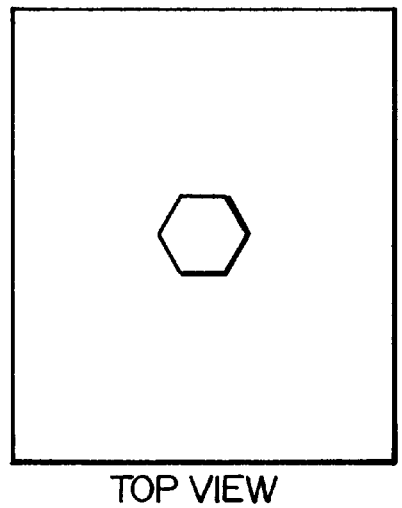

THE DIRECT (FIRST) ARRIVAL OF THE ELECTROMAGNETIC WAVE ALONG A PIPE WITH THE RADIUS OF $r_0$

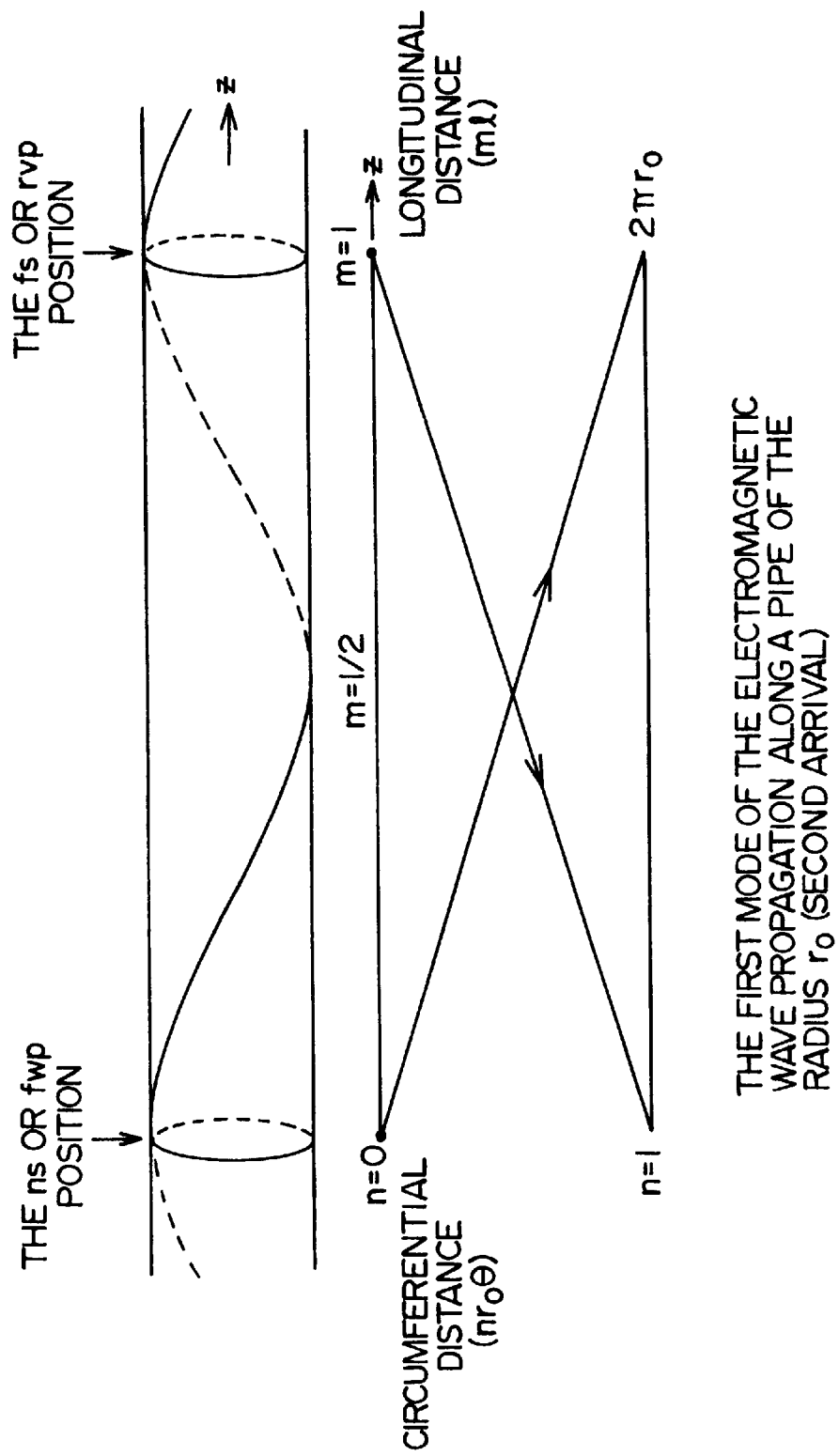

THE 2ND MODE OF ELECTROMAGNETIC WAVE PROPAGATION ALONG A PIPE WITH THE RADIUS $r_o$ (THIRD ARRIVAL)

THE ns OR fwp PROFILING

THE fs OR rvp PROFILING

THE HELICOIDAL WAVE PATHS FOR THE
ns OR fwp AND fs OR rvp POSITIONS

PIPE TESTING APPARATUS AND METHOD USING ELECTRICAL OR ELECTROMAGNETIC PULSES TRANSMITTED INTO THE PIPE

This application claim benefit to Provisional application 60/012,336 and filing date Feb. 27, 1996.

BACKGROUND OF THE INVENTION a) Field of the Invention

The present invention relates to a system, apparatus and method for testing elongate objects, such as pipe, pipeline, as well as storage tank, etc., and is directed toward the problem of detecting corrosion, and/or defects, and/or other anomalies to the pipe or pipeline under conditions where access and/or visual or instrumental inspection of the pipe or pipeline is either limited, not possible, or impractical.

b) Background Art

In petroleum processing and petrochemical plants and other industrial environments, it is common to have numerous pipes extending between various locations in the plant, with these pipes carrying fluid or gas (e.g.,petroleum products), often under intensive heat and high pressure. Likewise, trans-continental and interstate oil/gas pipelines under even higher pressure extend hundreds and thousands miles.

Similarly, pipelines carry toxic and non-toxic wastes, and storage tanks store high pressure gas and other volatile petroleum products, etc. These pipes or pipelines are invariably made of steel and can have an inside diameter ranging anywhere from two to sixty inches, or even outside of this range. The exterior of these pipes or pipelines are often insulated, and shielded with the insulating and metallic shielding layers being as great as approximately ⅛ to 5 inches or more in thickness, or outside of this range. Moreover, these pipes or pipelines are interconnected by joints, elbow joints, flanges, etc., while their geometrical configurations of the layouts are complex.

For a number of reasons, (safety, environmental potential hazards, avoiding costly shut-downs, etc.), the integrity of these pipes or pipelines must be preserved. Corrosion and/or defects in the pipe or pipeline can occur for a number of reasons. One is that moisture condensates can collect between the insulating layers and the pipe or pipeline, thus causing corrosion (i.e., rust). Visual inspection of the steel pipe that is encapsulated in insulation is not possible unless the layers of insulation and shielding are removed, and then replaced. This is expensive and time consuming, and as a practical matter it would be economically unfeasible to accomplish the inspections with reasonable frequency.

U.S. Pat. No. 4,970,467, Burnett, issued on Nov. 13, 1990. The method and apparatus in this patent are directed toward detection of corrosion in pipes and pipelines. Two pulses are transmitted into the pipe to travel toward one another, and these pulses intersect at an intermediate location. If there is corrosion at the location of the intersection, then this affects the pulses in a way which would be indicative of corrosion, and the resulting wave forms would differ from those which would result where the intersection of the pulses is at an uncorroded area of the pipe. By timing the transmission of the two pulses and shifting the transmitting timesin increments, the point of intersection can be stepped along the pipe or pipeline so that corrosion can be detected at various locations.

Also, there is a group of patents relating to detection of corrosion in pipelines, these being the following:

U.S. Pat. No. 4,839,593, U.S. Pat. No. 4,990,851, U.S. Pat. No. 4,929,898, and U.S. Pat. No. 4,926,986. Three of these issued to Brian R. Spies as inventor, and one to Pedro F. Lara as inventor. These patents deal with a transient electromagnetic method of detecting irregularities on container walls of pipelines by measuring wall thickness. Basically the inventors utilize transient electromagnetic probing called "TEMP", which allows the remote probing of a conductor by inducing a current into the conductor and analyzing the decay of current. It is the induced field with which these patents deal.

There is a fundamental difference between those four patents and the present invention. The method in those four patents is based completely on the quasi-static electromagnetic phenomenon, which is a different field and neglects the propagation field entirely with which the present patent application deals. It is stated that it is only the conductivity of the container which plays a role in the diffusion of induced field in the conductor, and they are measuring the decay of the induced diffusion field in the conductor.

The present invention fundamentally is completely different from the above mentioned four patents. The present invention deals with the complete dynamic electromagnetic phenomenon, which is about the dynamic aspects of electromagnetic wave propagation, reflection and refraction, and detraction, attenuation, dispersion, etc. It is the propagating field with which the present invention deals. The conductivity of the conductor is just one of the electromagnetic parameters. More importantly, the present invention deals with the permitivity which in essence controls the dynamic electromagnetic wave propagation. In the dynamic electromagnetic wave phenomenon, the conductivity enters into the attenuation of electromagnetic wave propagation, and the permitivity fundamentally governs the propagation field. Naturally, the present invention deals with permeability, and the permeability plays a role in both attenuation and propagation.

Other patents of possible interest will be cited in a prior art statement to be filed subsequently to the filing of the present application.

It is the object of the present invention to provide a means of inspecting pipes or pipelines under the in situ environments and circumstances that corrosion, and/or defects, and/or other anomalies can be detected with a relatively high degree of reliability, and that the various difficulties of inspection, such as those mentioned above, can be eliminated and/or alleviated.

SUMMARY OF THE INVENTION

The present invention comprises both a method and a system for identifying corrosion on an electromagnetically permeable elongate member, such as a pipe. It is the object of the present invention to provide such a system which is particularly adapted for ascertaining the presence and location of such corrosion under conditions where access and/or visual or instrumental inspection of the pipe is either limited, not possible or impractical. The particular application of the present invention is to detect corrosion on pipes or pipelines, and the present invention has been found to be particularly effective where the pipe or pipeline is either covered by insulation, buried underground, or being inaccessible when extending underneath a roadway.

The method of the present invention comprises transmitting electric or electromagnetic pulse into the elongate member in the transmitting location of the elongate member and at a transmitting time to cause the pulse to travel as the propagating electromagnetic wave to a receiving location over a travel distance and during a travel time interval. The electromagnetic wave is then received at a receiving time at the receiving location on the elongate member. Then any delay in said electromagnetic wave traveling over the travel distance is ascertained to determine the presence of corrosion on the elongate member.

The pulse has a sufficiently high frequency so that the electromagnetic wave travels over the outside surface of the elongate member at a very thin skin depth for corrosion on an exterior surface on the elongate member may be present. The receiving means is operatively positioned at the receiving location to receive the electromagnetic wave. The receiving means in one preferred form comprises an antenna responsive to electromagnetic radiation.

In one embodiment, the receiving means comprises a plurality of receivers which are operatively positioned at spaced receiving locations along the lengthwise axis of the elongate member. In this arrangement, the method further comprises:

a. ascertaining distances between said spaced receiving location;

b. ascertaining times of travel of said electromagnetic wave between said receiving locations;

c. ascertaining from said distances and said times of travel, velocity of said electromagnetic wave or waves between said receiving locations to identify presence of corrosion.

The method further comprises ascertaining an area or areas between two receiving locations where the velocity of the electromagnetic wave or waves is lower, to identify presence and location of corrosion.

In several preferred embodiments, there is provided a multi-channel cable, comprising a plurality of channels, and each of said receivers is operatively connected to a related one of the channels. The multi-channel cable directs signals received from the receiver to a data receiving location. In one arrangement, the multi-channel cable is a fibre-optic cable, and in another arrangement an electrically conductive multi-channel cable.

The pulse is transmitted to the elongate member by directing a pulse from a pulse generator to a transmitter at the transmitting location, with the transmitter in turn transmitting an electric or electromagnetic pulse into the elongate member at the transmitting location. The multi-channel cable transmits the received signal to a data acquisition signal analyzer means. Also, the pulse generator transmits a triggering signal to a data acquisition signal analyzer.

To accomplish both forward profiling and reverse profiling of the elongate member, the pulse is transmitted into a first end of a section of the elongate member which is under test, and this pulse is received at a second end location of the section of the elongate member. Then a second pulse or a set of pulses is transmitted from the second end of the section of the elongate member under test toward the first end of the section of the elongate member, where the signal is received and delivered to a data receiving location. In another embodiment, the transmitter is positioned at the transmitting location to transmit the pulse into the elongate member. The receiver is positioned sequentially at a plurality of spaced receiving locations along the elongate member. The pulses are transmitted into the elongate member for each receiving location at which the receiver is placed, and signals received by the receiver at the receiving locations is transmitted to a data receiving location. As indicated above, the present invention is particularly adapted for detecting a corrosion of a pipe having an insulating layer. In this instance, the method further comprises providing a receiver which is an antenna responsive to electromagnetic radiation. The receiver is placed adjacent to an outer surface of the insulating layer of the pipe to receive the electromagnetic wave. Also, the transmitter is placed by a portion of the insulation being removed at the transmitting location, and the transmitter is placed adjacent to the pipe at the transmitting location.

In one arrangement, the transmitter comprises an electrical contact member which is placed into direct contact with the pipe, and an electric current is transmitted to the transmitter. In another arrangement, the transmitter is a directional antenna, which is positioned adjacent to the pipe. An electric pulse is transmitted to the antenna which in turn transmits an electromagnetic pulse into the pipe. In one arrangement, the receiving means comprises a plurality of antennas which are placed adjacent to the insulation of the pipe at a plurality of the receiving locations.

In another embodiment, there is a plurality of transmitters which are spaced circumferentially from one another at the transmitting location. A plurality of electric or electromagnetic pulses are transmitted from these transmitters into the elongate member, either sequentially, simultaneously, or both simultaneously and sequentially toward a receiving location or locations.

Also, in another arrangement there is a plurality of receivers at the receiving location which are spaced circumferentially from one another. Pulses are transmitted as electromagnetic waves from selected transmitters to the receivers at the receiving location in selected patterns.

In the system of the present invention, the transmitting means comprises a one or a plurality of transmitters, as described previously in this text, and one receiver or a plurality of receivers. Also, there is provided a means to ascertain a time interval of travel of the electromagnetic wave from the transmitting location to the receiving location.

Also, the system comprises means to ascertain intervals of travel time between various pairs of two receivers to identify where the velocity of the electromagnetic wave or waves is lower.

As described above, several embodiments of this system comprise multi-channel cables.

Other components and functions of the system of the present invention are disclosed in the previous text in this "Summary of the Invention", and also it will be apparent from the following detailed description.

BRIEF DESCRIPTION OF THE DRAWINGS

FIGS. 1c and 1d are schematic drawings corresponding to FIGS. 1a and 1b but showing a second embodiment;

FIGS. 2a and 2b are schematic drawings similar to FIGS. 1a and 1b, but showing a third embodiment of the present invention (and also showing the basic system for a fourth described embodiment which is described verbally).

FIGS. 3a and 3b are two schematic drawings illustrating a fifth embodiment of the present invention;

FIG. 4 is a schematic arrangement with matching pairs of transmitters and receiver for measuring interval differences;

FIG. 6a and 6b are sectional views showing first and second plural antenna arrangements;

FIG. 7 is a graph illustrating operating features of the present invention.

FIGS. 8a, 8b and 8c are side, bottom, and top views of a transmitter that is magnetically attached to the pipe;

FIG. 9b is an isometric view and also a laid out two dimensional view of an electromagnetic propagation wave of a second arrival along pipe (in the isometric view) and two second arrivals (in the two-dimensional view);

DESCRIPTION OF THE PREFERRED EMBODIMENTS

It is expedient that we first introduce the present invention through the basic techniques of detection of corrosion, and/or defects of a pipe or pipeline under test, the operations, the underlying phenomena, the relevant devices developed, and the methods of analysis and interpretation with all the relevant supporting documents and for the use of a variety of hardware including multi-channel cable and single-channel cable, source and receiving antennas that would set the stage of what follows.

FIGS. 1a 1b, 2a and 2b, and 3a and 3b are basic schematic diagrams of the System of the present invention being in its operative position where it is being used in testing; as an example, a segment of an insulated pipe or pipeline, beginning with a multi-channel receiving cable. All the other relevant figures pertaining to the present invention are all included herein.

The present invention is applicable to global and detailed detection of corrosion and/or defects in a pipe or pipeline in terms of the integrity of a segment of a pipe or pipeline under test as a whole, or the location and the degree of its corrosion and/or defects in details, respectively. In the sequel, corrosion and/or defects are referred to as "corrosion," and corrosion under insulation in a pipe or pipeline as "CUI."

Global detection is here referred to as detecting the overall integrity of an extended length of pipe, say greater than 25, 50, . . . , hundreds, or even thousands of feet in length, and rank the overall integrity of the pipe or pipeline in A, B, C and D, ranging from good, moderately good to poor and very poor, respectively.

Detailed detection is here referred to as detection of the location of corrosion within +/– two feet and the degree of corrosion in terms of their severity to be classified into 1, 2, 3, and 4, ranging from good, moderately corroded, corroded, and severely corroded in the pipe or pipeline in question.

Figure 1A:
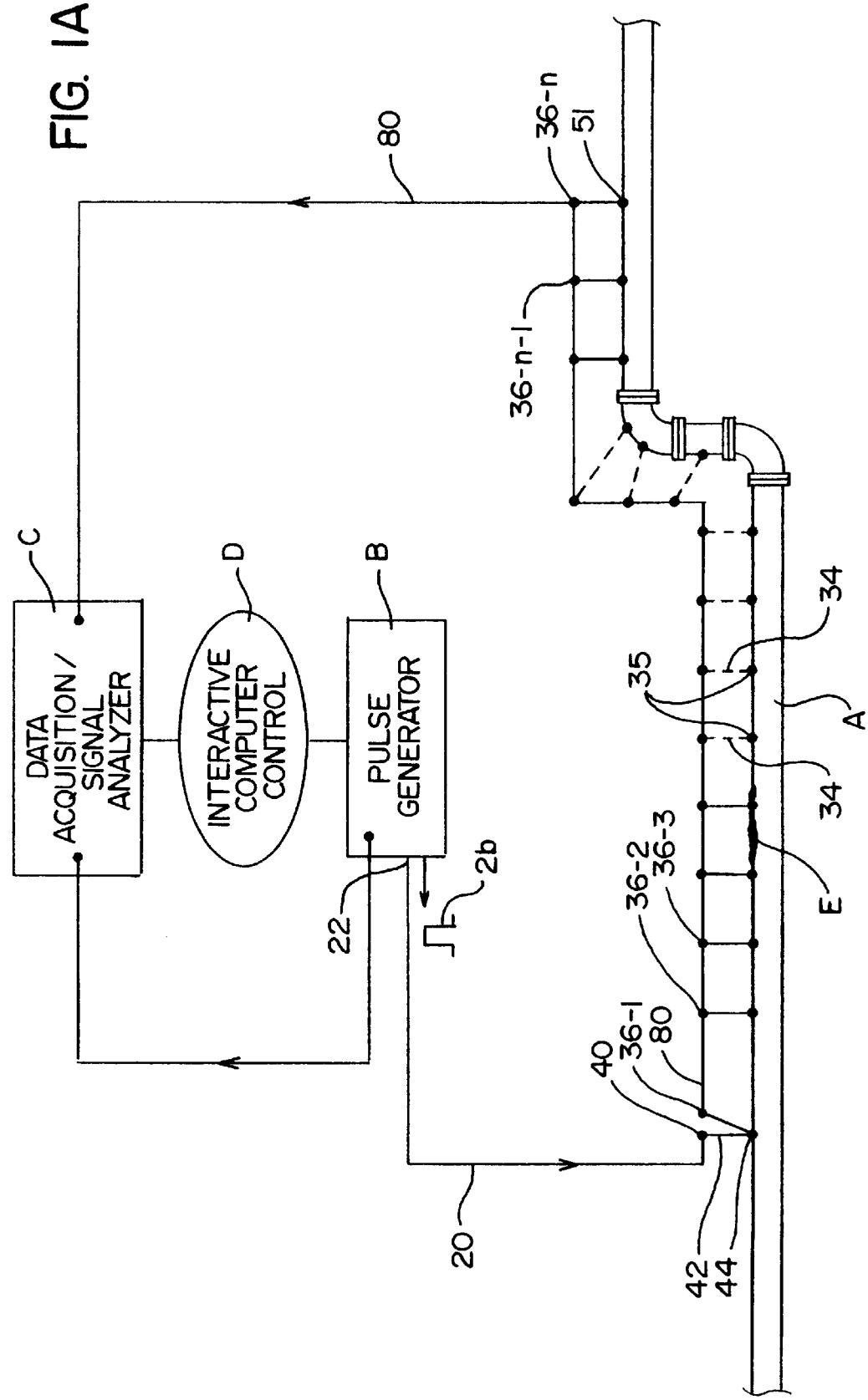
FIGS. 1a and 1b are schematic drawings of a first embodiment of the present invention, with FIG. 1a showing the system in a forward profiling mode, and FIG. 1b showing the system in the reverse profiling mode.
Figure 1B:
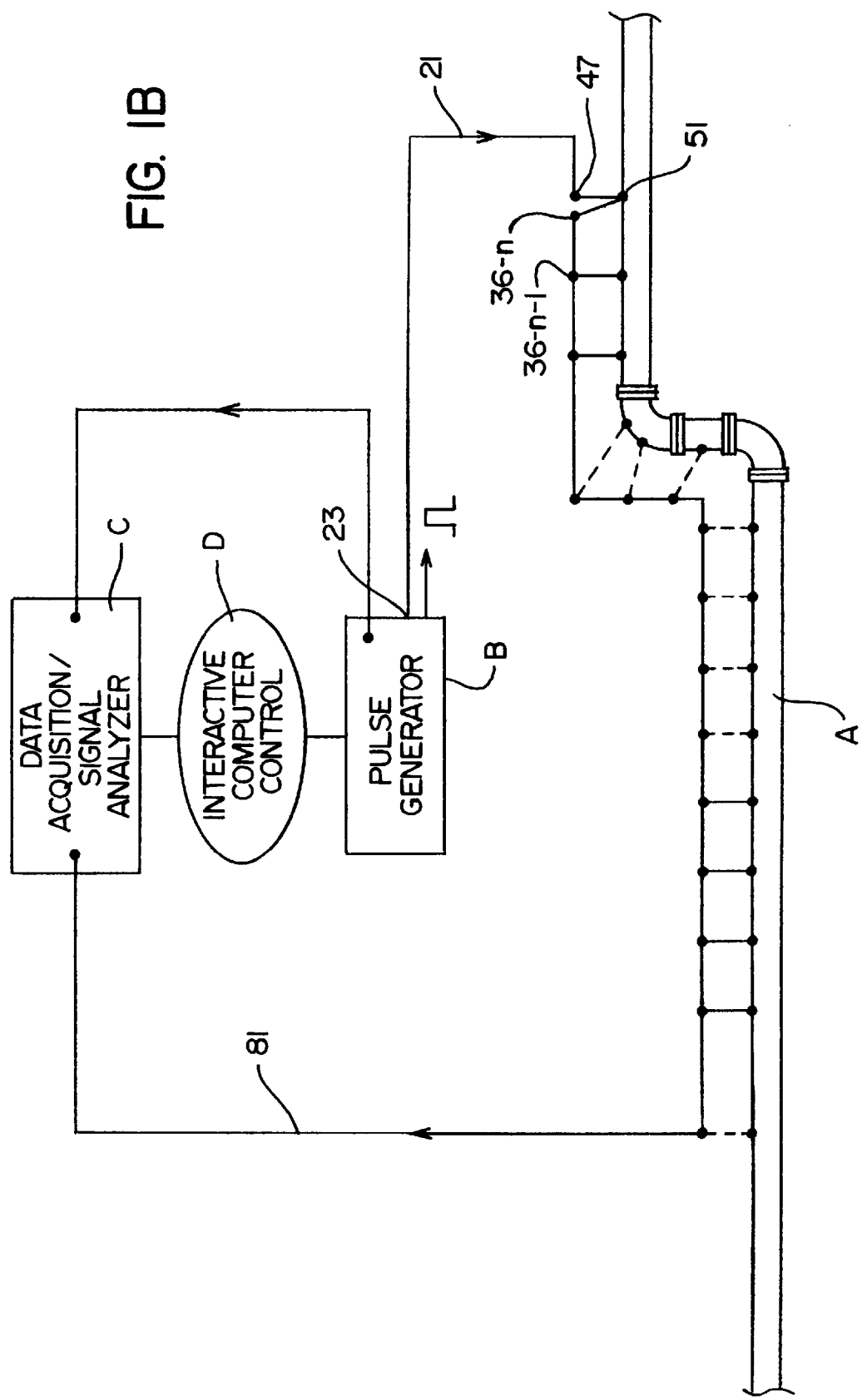

Global Detection:

With reference to FIGS. 1a and 1b, for global detection of corrosion, the source is placed at the ns (near-side) or fwp (forward-profiling) position and the only receiver is placed at the fs (far-side)or rvp (reverse-profiling) position of the pipe or pipeline. The source is an electric pulse of an optimal width, which is generated by a pulse generator. The electric pulse excites the source cable and is propagated through the source cable, and in turn is propagated along the pipe or pipeline as an electromagnetic pulse (or waves)to be received at the fs or rvp position. It is understood that the propagation of an electric pulse through the cable(s) and the pipe or pipeline no longer in the classic sense remains an electric pulse but an electromagnetic pulse, as the electric and magnetic fields are always coupled in a medium other than in an idealized free space. For establishment of a reversed profile, the measurement is then reversed, i.e., the transmitter is now located at the fs or rvp position and the only receiver is placed at the ns or fwp position. Again, if the source transmitter and the receiver are located exactly in line longitudinally, the first arrival of the electromagnetic waves will take a straight line path parallel to the axis of the pipe or pipeline. For global detection, the subsequent arrivals will all take helicoidal paths; the number of turns of the helicoidal paths depend upon the mode of the propagation of the electromagnetic waves. There are no measurements taken between the ns or fwp and the fs or rvp positions for global detection.

Detailed Detection:

For detailed detection of corrosion in a pipe or pipeline, the source or transmitter is first placed at the ns or fwp position and the receivers are placed in a regular, irregular or combination of regular and irregular n intervals between the ns and the fs positions.

For the ns or fwp operation, the transmitter at the ns or fwp position is excited by an initial electric pulse, which is transmitted through the source cable, and the receiving antennas are directed at the pipe or pipeline with reference to the ns or fwp position as the nearest channel and the fs or rvp position as the furthermost channel. The numbering system of the n channels between the ns or fwp and fs or rvp positions, therefore, is preferably in sequence for the convenience of tracking, while the first channel is at the ns or fwp position and the n-th channel is at the fs or rvp position. The rest of n-2 channels are distributed between the ns or fwp and the fs or rvp positions.

For the fs or rvp operation, an identical transmitter for the ns or fwp operation is then excited at the fs or rvp position for an initial electric pulse generated from a pulse generator. The numbering system of the n channels remains unchanged except measuring starts from the nth channel at the fs or rvp position backward toward the first channel at the ns or fwp position.

For global as well as detailed detection of corrosion in a pipe or pipeline, reference pipes or pipelines are given, about which the detailed conditions of corrosion are known. Under the same given environment, the overall integrity and the detailed location and degree of the localized corrosion of the pipes or pipelines in question are calibrated against these reference pipes or pipelines.

EMBODIMENT ONE: Single-Pulse/Multi-Channel Receivers:

With the preceding introduction, and reference to FIGS. 1a and 1b, there is shown a segment of the pipe A which is under test. In this instance, this segment of the pipe A is or may be a section of a pipe or a pipeline that would typically be used in the petroleum, chemical, utility, petrochemical, and/or the like industry, where the pipe or pipeline is made of steel and surrounded by a coat and/or a layer of insulation and a layer of aluminum, galvanized steel, or other metallic shield.

The apparatus or system of the present invention is generally designated for the ns(near-side) or fwp(forward profiling) operation (FIG. 1a), and the fs(far-side) or rvp (reversed profiling) operation (FIG. 1b). It comprises a pulse generator B, a data acquisition/signal analyzer (D/S) C, an interactive computer D, and a source cable 20 or 21, and a multi-channel receiving cable 80 or 81. The source and receiving cables can be electric but they must be highly radiation shielded in order to avoid mutual interference and high energy loss primarily due to radiation. In the sequel, it is completely understood that all the cables, either the source, receiving, or any other cables including all the leads, used in conjunction to the present invention, all are of highly radiation-shield type with a minimum radiation loss.

For the ns or fwp Operation:

Reference is first made to FIG. 1a to describe this mode of operation. A triggering pulse from the pulse generator B first triggers the data acquisition/signal analyzer C to provide the initial activation time of an electric pulse to be generated by the pulse generator B. The source cable 20 is a single-conductor source cable with one end 22 being connected to the pulse generator B. A prescribed optimal electric pulse with a low repetition rate either a wide-open pulse width or a very narrow pulse width 26 excites the end of the source cable at 22 and is then propagated from the end 22 through the cable 20 to the termination of the cable 40, which is connected to the transmitter 44 with a radiation-shield electric lead 42. In the present invention, the transmitter 44 is a switch-on/off super magnet or a directional antenna (such as shown in FIGS. 6a and 6b.) It can be any other fidelity devices, such as cross-dipole, two-component dipole, or various specially designed antennas, etc. The contact of the transmitter to the pipe or pipeline A is made by the removal of a small area of the insulated cover from the pipe or pipeline. For the switch-on/off super magnet type of transmitter, the contact surface of the steel pipe or pipeline in a dimension of 2 inches×2 inches is roughly polished to insure a good contact with the super magnet when it is turned on. For the transmitting antenna type of transmitter, there is no need to have the surface of contact on the pipe or pipeline A prepared.

The receiving cable 80 is a multi-channel electric cable, which is connected to the D/S C. The interactive computer D has operative control connections to both the D/S C and the pulse generator B as shown in FIG. 1a.

The receiving cable 80 thus has n connecting ports, 3-1, 36-2, . . . 36-n, which are spaced in n intervals along its length. The n receivers, each of which is either a single directional antenna 35, or a group of directional antennas 35, are directed at the pipe or pipeline A in corresponding n intervals. Each antenna 35 has a lead 34, which is connected to the respective connecting port of the receiving cable 80, namely, 36-1, 36-2, . . . 36-n along the length of the pipe or pipeline A under test. As indicated above, this cable 80 is a multi-channel cable and has a plurality of discrete wires, one for each channel, extending along its entire length, with each wire in the cable 80 being connected electrically to the steel pipe directly by a special sensor such as the switch-on/of super magnet or by indirectly such as an antenna device.

In the present embodiment of detecting CUI, the receiving sensors or receivers are either directly placed on the very external metallic shield of the pipe or pipeline, or indirectly by directing the directional antenna 35 or a group of the directional antennas 35 at the pipe or pipeline A without stripping off any insulation.

In describing the operation of the present invention, a ns or fwp position 44 and a fs or rvp position 51 are established as the starting receiving position 44, and the end of the receiving position 51 of the segment of the pipe or pipeline under test, respectively. In the somewhat simplified drawing of FIGS. 1a and 1b, there are shown only a few contact points. For purpose of description, some of these contacts have been given sequential numerical designations. (36-1, 36-2, 36-3, etc.).

In operation, an electric pulse of a predetermined optimum width and an optimal repetition rate is generated by the pulse generator B, from the point 22 is propagated through the source cable 20, and is applied to the transmitter 44 at the ns or fwp position as the source excitation of the pipe or pipeline A. This pulse, now the electromagnetic pulse (or waves), propagated through the source cable 20, then travels along the pipe or pipeline past the various receiving connecting points 36 along the length of the pipe segment under test. This signal is then received by the receiving sensors, namely, the passive antennas 35 at the various connecting locations 36-1, 36-2 . . . 36-n and recorded digitally through an A/D converter by the D/S C and preprocessed. The recording will be multiplexed and subsequently demultiplexed. The manner in which these signals are received, processed and analyzed will be described later herein.

To discuss the operation of this System further, let it be considered that an electromagnetic pulse, after the electric pulse transmitted through the source cable to become the electromagnetic pulse (or waves), is to be received at the receiving point 36-1 which is precisely at the ns or fwp position of the transmitter 44, i.e., the position of the receiver coincides with that of the transmitter. The D/S C, which is being controlled by the interactive computer D, is set so that it will respond to the signal coming through the first channel of the multi-channel receiving cable that is connected to the contact point 36-1. As the transmitter 44 emits an electromagnetic pulse (or waves) at the ns or fwp position, it is immediately received by the receiver 36-1 without any time delay. Actually there is a very minute time delay, because the receiver can only be placed adjacent to the transmitter, unless the transmitter can also function as the receiver at the same location. The electromagnetic pulse, which is emitted by the transmitter, is then propagated along the pipe or pipeline A forwardly toward the fs or rvp position and backwardly in the opposite direction. Only this propagating pulse toward the fs or rvp position pulse is received along the pipe or pipeline at the receiving points 36-1, 36-2, 36-3, . . . 36-n, respectively. Each channel has its own electric cable.

For purposes of description, a given single channel of the multi-channel cable 80 shall be considered as comprising several sections. It must be viewed that the source cable 20 is independent of the receiving cable, which in the present case is the multi-channel cable 80. Once the initial electric pulse generated from the pulse generator B, it is transmitted into the cable at 22 and through the source cable 20 to the transmitter contact point 44. As the electromagnetic pulse impinges on the pipe or pipeline A, it is propagated along the pipe or pipeline A through the section 80 to the D/S at 80a. This pulse is sensed by all the receivers distributed along the pipe or pipeline A under test. As the D/S C is set, it is responsive to the signal received at the receiving points, 36-1, 36-2, . . . . 36-n. The received signals from each channel are transmitted through each respective channel of the multi-channel cable 80 and, in turn, transmitted to the D/S C to be recorded and also the information will be transmitted to the interactive computer D.

For the fs or rvp Operation:

Reference is made to FIG. 1v to describe this second mode of operation. With this above described process having been completed, then the same process is repeated, but in reverse (FIG. 1b). More specifically, an electric pulse is now generated from the pulse generator B, which is propagated through the source cable 21 to the end of the cable 47. The end 23 of the source cable 47 is connected to the transmitter 51 with an electric lead 49, which is an active source antenna for the reversed profiling operation. As before in the ns or fwp operation, the pulse generator B triggers the D/S C and in turn to activate the initial time of the electric pulse.

Thus, the electric pulse is delivered from one of the end of the cable 23, which is connected to the pulse generator B. The pulse is propagated through the source cable 21 and excites the pipe or pipeline by the transmitter at the fs or rvp position 51. The D/S C is set so that it responds to the pulse, which is sensed by the receiver at the receiving point 36-n, which is now at the fs or rvp position 51. The pipe or pipeline A at the contact point 51 is similarly prepared as in the ns or fwp operation for the mounting of the source transmitter; for instance, as previously described for the ns or fwp operation, mounting of a switch-on/off super magnet or a transmitting antenna. Thus, this pulse, as an electromagnetic pulse (or waves), is propagated through the source cable 21 into the pipe or pipeline A. It is then transmitted along the pipe or pipeline A at the receiving contact points 36-n . . . , 36-2, 36-1 in the reverse order of that for the ns or fwp operation. And it is transmitted through its respectively related channel, through the intermediate cable section 81 and thence travels through the cable section 81 to the receiving point 81a and thence into the D/S C to be recorded. The data acquired and the information developed by the D/S C relative to this pulse are then transmitted to the computer D and stored.

Thus, as described above, the receiving locations 36 are stepped along the length of the pipe or pipeline proceeding from a location at the receiving contact points, 36-n at the fs or rvp position 51 all the way to the initially starting contact point 36-1, which is at the ns or fwp position.

Figure 1D:
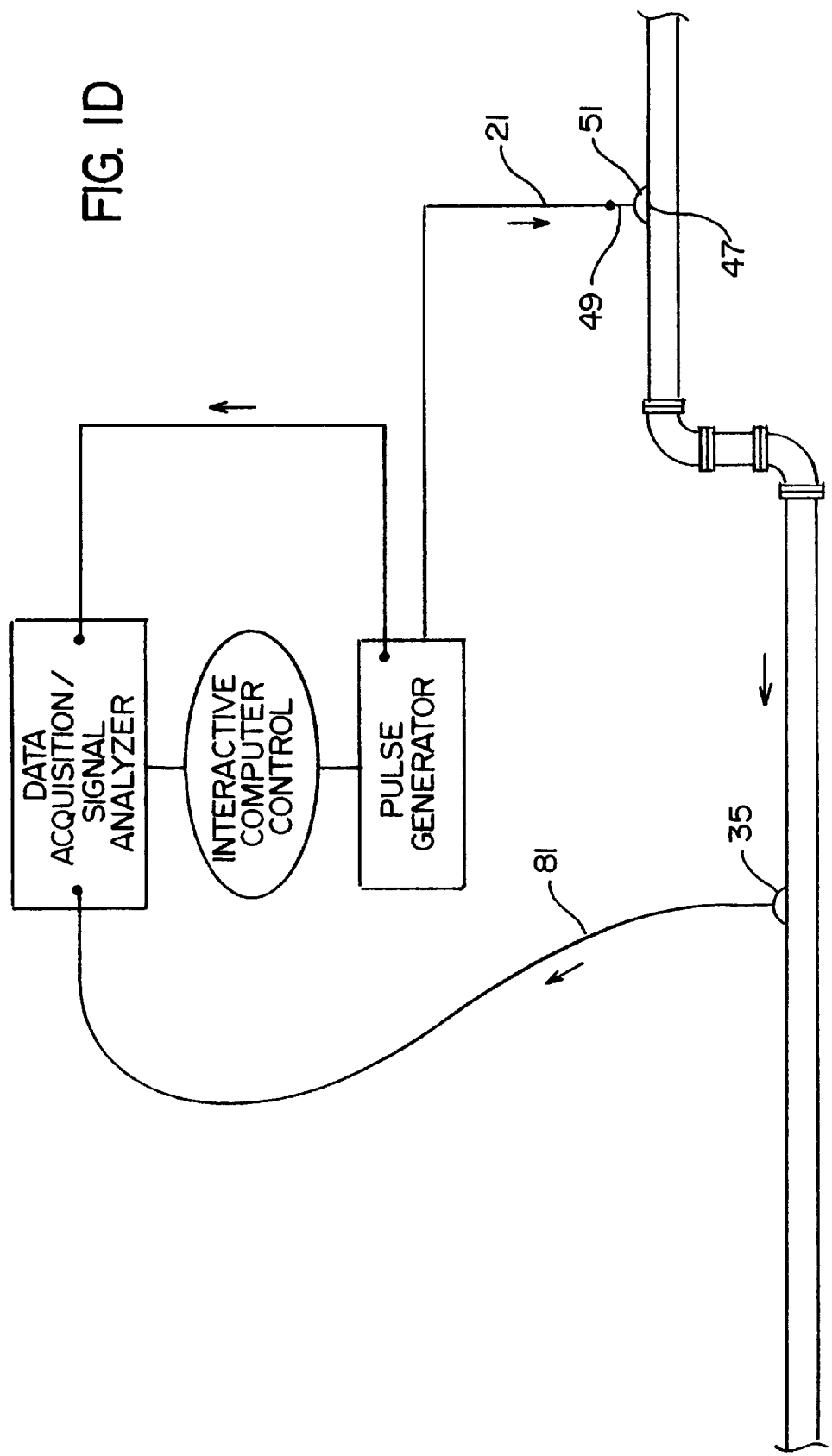

EMBODIMENT TWO-Single-Pulse and Single-Channel Receiver:

This second embodiment will be described with reference to FIGS. 1c and 1d. Because of certain operational restrictions, field measurements sometimes call for a single-conductor single-channel receiving cable, as shown and described in this second embodiment.

For both the ns or fwp operation and the fs or rvp operation, the operational procedure basically remains the same as in the first embodiment where there is used a multi-channel receiving cable, except that a single-channel receiving cable 80 is used in place of the multi-channel receiving channel. Thus, the single-channel receiving cable is now only able to handle one receiving location at a time. It is now necessary that this single-channel receiving cable be moved each time after each measurement at each receiving location.

As in the first embodiment two single-conductor source cables 20 and 21 are still used as the source cables for both the ns or fwp and the fs or rvp operations, respectively. A switch-on/off super magnet or a directional antenna 44 or 51 is affixed to the end of the source cable at the connecting points 42 or 47, through the leads, 42 or 49, respectively. As a precaution, the source cable is separated from the receiving cables as far as possible at a permissible distance. For the ns or fwp operation, the transmitter 44 is thus positioned at the ns or fwp position, but there is only one receiving antenna 35, which is positioned at the end of the receiving cable 80. This receiving antenna 35 is physically moved at sequential increments of distance starting from the ns or fwp position toward the fs or rvp position.

For example the antenna 35 can be first positioned at point 36-1 to receive a signal from one pulse, moved then in point 36-2, next point 36-3, etc.

For the fs or rvp operation, the transmitter is positioned at the fs or rvp position while the receiving antenna, which is positioned at the end of the receiving cable, is moved from the fs or rvp position backward toward the ns or fwp position at n intervals of distance.

The single-conductor single-channel receiving cable 80 for the ns or fwp operation and the receiving cable 81 for the fs or rvp operation are used, respectively. One end of the receiving cable is connected to a receiving antenna, and the other end is connected to the D/S C for either the ns or fwp or the fs or rvp operation, respectively. For the ns or fwp operation, the source is located at the ns or fwp position, 44 and (as indicated above) the receiving antenna is moved forward along the pipe from the ns or fwp position 36-1 which coincides with the position of the transmitter 44 to the fs or rvp position 36-n at an n interval of distance. Then the operation of a reversed profiling is carried out. Now the transmitter excites the pipe or pipeline A at the fs or rvp position and the receiving antenna, after receiving and recorded the signals, is moved backward from the fs or rvp position 36-n to the ns or fwp position 36-1 at an identical n interval of distance as used in ns or Fwp operation of the forward profiling.

Alternatively, instead of repeating measurements at a receiving location twice, once for the ns or fwp operation and the second time for the fs or rvp operation, for convenience, the above measuring procedures can be accomplished in one step. When the receiving antenna at a given location is completed for the ns or fwp operation, the receiving antenna is kept at the same receiving location acting as the receiver for the fs or rvp operation. Therefore, the receiving antenna at a given receiving location needs to be moved only once to accomplish both the ns or fwp and the fs or rvp operations.

EMBODIMENT THREE-Single-Pulse and Multi-Channel Receivers with Fiber-Optical Source and Receiving Cables Reference is now made to FIGS. 2a and 2b. To provide further reduction of the electromagnetic radiation and interference due to the source and receiving cables, in this third embodiment two single-channel fiber-optical source cables and a multi-channel fiber-optical receiving cable can be used. However, an electrical-to-optical converter and an optical-to-electrical converter are needed at every junction of the electrical cable and the fiber-optical cable wherever an fiber-optical cable replaces an electrical cable as shown in FIGS. 2a and 2b, which are to be compared with FIGS. 1a and 1b, respectively. Notice in FIGS. 2a and 2b that where the electrical cables are replaced by the fiber-optical cables, the fiber-optical cables are marked by a double-line.

Components of Embodiment Three which are similar to components of Embodiment One and Two, except the electrical source and electrical multi-channel cables, are now replaced by the fiber-optical source cable and the fiber-optical multi-channel receiving cables, respectively. One will be given like numerical designations, with an "a" suffix distinguishing those of Embodiment Three. This third embodiment comprises essentially a pulse generator B, a data acquisition/signal analyzer (D/S) C, and also an interactive computer control D, which remain unchanged.

However, instead of having (as in Embodiment One and Two) a multi-channel cable 80 having a plurality of discreet electrical wires, there is provided a ns or fwp profiling multi-channel fibre-optical receiving cable 86a extending between the connecting location 36-1 to the connecting location 82a. Also, there is a fs or rvp profiling fiber-optical receiving multi-channel cable section 81a extending from the end location 83a to the connecting location 47a.

The two source cables 20a and 21a are now made as fiber-optical cables. Between the fiber-optical source cable 20a and the connecting location 40a, there is provided an optical-to-electric converter 72, which is mounted on the upper of plate of the four-post standoff of the transmitting antenna schematically shown as 42a that converts the pulse or signal from the fiber-optical cable 20a to an electrical signal which excites the transmitting antenna 44a. Also, there is an electrical-to-optical converter 72 between the points 22a and 26a.

As Embodiment One and Two, a triggering pulse from the initial pulse generator B triggers the D/S C to initiate the activation time of the electric pulse.

The initial electric pulse is transmitted from the point 22a of the pulse generator B and is converted by the electrical-to-optical converter 72 to an optical pulse or signal that travels through the source cable 20a to be converted back to an electrical pulse by an optical-to-electrical converter, which is mounted on the top of the transmitting antenna marked as 42a. In turn, this now electromagnetic pulse is received by the receiving antennas 35a, along the pipe or pipeline, from 36-1a, 36-2a , . . . 36-na, each of which has an electrical-to-optical converter on the top of the receiving antenna, and again converts the electromagnetic signals to optical back to the optical multi-channel optical receiving cable 80a to be transmitted to an electric-to-optical converter 76a, which is connected between each channel location 36-1a, 36-2a, . . . , 36-na individually and the optical cable section 80a and back to the D/S C.

In like manner, during the fs or rvp operation see FIG. 2, the electric pulse from the pulse generator B is converted to a fiber-optical signal by an electric-to-optical converter 73a that is between the points 25a and 29a. The fiber-optical signal travels through the fiber-optical cable section 20a to the optical-to-electric converter 51a, which is mounted on the top of the transmitting antenna 53a. The manner in which the rest of the process is accomplished is substantially the same as described above relative to the fs or rvp operation as in the ns or fwp operation so this will not be described further herein.

However, it is fitting to mention that it is also feasible that all the data be transmitted and recorded as data string through a single fiber-optical cable rather than each channel having its own separate cable. The data acquired and the information developed by the D/S C from the receivers are then interactively communicated to and stored in the computer D.

Embodiment three may under certain circumstances provide certain advantages. For example, by the use of fiber-optical cables, the effects of creating unwanted electromagnetic interference due to natural induction, radiation, and coupling are effectively minimized or eliminated.

EMBODIMENT FOUR-Single-Pulse and Single-Channel Receiver with Fiber-Optical Source and Receiving Cables.

Both the ns or fwp operation and the fs or rvp operation of the present embodiment is exactly identical to as Embodiment Two, except the electrical source and receiving cables are now replaced by the fibre-optical source and the fibre-optical receiving cables. The components of the hardware, including the pulse generator B, the data acquisition/signal analyzer (D/S) C, and the interactive computer D are shown as FIGS. 2a and 2b and, remain unchanged. With reference to Embodiment Three, the only difference is that the optical multi-channel receiving cable of Embodiment Three is now an optical single-channel receiving cable. Moreover, the locations of the converters, the electrical-to-optical and optical-to-electrical, also remain the same.

Therefore, for both the ns or fwp and the fs or rvp operations, the optical single-channel receiving cable is moved upon completion of each measurement.

EMBODIMENT FIVE-Dual-Pulse and Single-Channel Receiver.

Embodiments One through Four are all dealing with the single-pulse techniques that are based on the excitation of a single source pulse. For example, the transmitter used is either a switch-on/off super magnet, which is directly affixed to the pipe or by a high-pass directional antenna directed at the pipe or pipeline under test.

Embodiment Five here is dealing with an improved dual-pulse technique, while its basic concept remain unchanged. (See U.S. Pat. No. 4,970,467, issued in Nov. 13, 1990).

In the earlier version of the dual-pulse techniques, the intersection of the two traveling pulses from the ns or fwp position and from fs or rvp position along the pipe or pipeline A was established at either ns or fwp position or the fs or rvp position, where the super magnet was mounted.

In the present improved dual-pulse technique, as shown in FIG. 3a, for efficiency, the two identical source transmitters at the ns or fwp 44 and the fs or rvp 51 positions of the pipe under test now can use either a switch-on/off super magnet or a directional antenna. Furthermore, by using a directional antenna, the receiving signals at the location of the two-pulse intersections between the ns or fwp and the fs or rvp potions can be tapped so that experimentally the wave forms of the effect of the intersection are observed.

The following gives a detailed description of the improved dual-pulse techniques.

As in Embodiments One through Four, a triggering pulse is delivered from the pulse generator B to trigger the D/S C so that the initial time of activation of an electrical pulse to be generated by the pulse generator B is referenced.

For global and detailed detection, two identical transmitters at the ns or fwp and the fs or rvp positions 44 and 51, respectively, are simultaneously excited but any time delay, thus, can be imposed on either of the two sources at 44 and 51 to allow the two pulses to be propagated in the opposite directions within the segment of the pipe or pipeline A under test to intersect at any desired locations along the pipe or pipeline. These two source transmitters can be two high-pass transmitting antennas (See FIGS. 5a and 5b) developed concurrently for the present invention, or two switch-on/off super magnets. A directional receiving antenna can be directed at the pipe or pipeline A anywhere between the ns or fwp and the fs or rvp positions. In practice, the receiving antenna is preferably to be located close to or at the source positions 44 and 51, for the fs or rvp operation and the ns or fwp operation, respectively.

For the ns or fwp operation, an initial intersection of the two identical but oppositely propagated pulses at the location of the receiving antenna, say at 36-n-1, is first established by adjusting the time delays of the two electromagnetic pulses, which are transmitted through the source cables 20 and 21 to the transmitters at the locations 44 and 51. Once the initial intersection of the two pulses is established at the receiving location, 36-n-1, the time delays for the two transmitters at the ns or fwp and the fs or rvp positions are thus fixed. Data are taken of the wave forms, including the first and subsequent arrivals, at the receiving location 36-n-1 each time by an incremental decrease of the time delay for the transmitting electromagnetic pulse from the ns or fwp position so that the two electromagnetic pulses would be intersecting between the transmitting location at the ns or fwp position and the receiving antenna location 36-n-1.

For the fs or rvp operation, the operation is then reversed and the same procedure repeated, the receiving antenna is now moved to the receiving location, say 36-2, to find the intersection of the two electromagnetic pulse, which are propagated from both the ns or fwp transmitting position and the fs or rvp transmitting position. Then the delay times for both the fs or rvp position and the ns or fwp position are fixed exactly at the time of the two pulses intersection at the receiving location 36-2. Data of the wave forms are then taken at the receiving location 36-2 by a desired incremental decrease of the time delay of the electromagnetic pulse propagated from the fs or rvp position toward the ns or fwp position such that the intersections of the two pulses would be between the fs or rvp position and the receiving location 36-2.

It is apparent that the dual-pulse operations in Embodiment Five for a single-channel receiving cable assume that the two electromagnetic pulses would intersect at the prescribed location. If the conditions of corrosion are complex, containing a variety of irregular distribution of corrosion within the segment of the pipe or pipeline under test, the precise location of the intersections of the two electromagnetic pulses at a given location could be shifted from the expected location of the intersection.

Thus, as an alternative to obtain greater precision, a multi-channel receiving cable can be used to replace the single-channel receiving cable 80 or 81 (FIG. 3b). Data can be taken at every receiving location as designated between the ns or fwp and the fs or rvp positions. The intersections of the two electromagnetic pulses can be observed experimentally. As required, the intersections of the two electromagnetic pulses on the basis of experimental observation can now be adjusted by the interactive computer B by means of the time delays of the two electromagnetic pulses. The actual intersection of the two electromagnetic pulses would give the precise information of the location and the degree of corrosion in the segment of the pipe or pipeline A under test. It is clear that at every receiving location, a data set of the intersection time of the two pulses along the pipe or pipeline at an incremental time delay are provided. These time delays of the intersection can be translated into distances for identification of the location and the degree of corrosion along the segment of the pipe or pipeline. Therefore, all the data sets for all the receiving locations would provide the redundant sets of data, which can be stacked and manipulated according to the locations of the receivers and the intersection times to yield the travel time information and the modification of the wave forms due to corrosion.

The operational procedures for a multi-channel receiving fiber-optical cables for both the ns or fwp and the fs or rvp operations are exactly similar to the single-channel receiving cable as in Embodiment Five, not to be re-described herein.

EMBODIMENT SIX-Single Pulse and Two Ended Multi-Channel Receiving Cable

Furthermore, the multi-channel receiving cable can be made into a two-ended receiving cable. Since the multi-channel receiving cable 80 or 81 is a passive receiving cable, which can be made into a two-ended cable with multi-channel connecting ports in the middle. One of the ends extends from the multi-channel cable 80 to the D/S C, while the other end extends from the multi-channel cable 81 to the D/S C. For the ns or fwp operation, the transmitter excites the pipe or pipeline at the ns or fwp position 44 so that the electromagnetic pulse, which is originated from the pulse generator B and propagated through the source cable 20, is propagated along the pipe or pipeline under test. The receivers, which are located at 36-1, 36-2, . . . 36-n along the pipe or pipeline, sense the signals. The D/S C is then set and records the signals for each receiving location through the channel cable 80. For the fs or rvp operation, the test settings for the ns or fwp operation remain the same. Now, instead the electromagnetic pulse, which is originated from the pulse generator B and propagated through the source cable 21, is propagated along the pipe or pipeline in the reversed direction from the ns or fwp operation. The receivers, which are located at 36-n, 36-n-1, . . . 36-1, sense the electromagnetic signals. The D/S C is set for recording the signals for each receiving location through the receiving channel cable 81 in the reversed order.

Travel Time and Wave Forms or Wave Trains:

It should be understood that the various components of the System would have previously been calibrated so that each relevant time increment in the system has already been predetermined. For example, with reference to FIGS. 1a and 1b, the time during which the pulse generator B generates a pulse at 22 and this pulse arrives at the connecting point 44 would have already been precisely measured, and this information is stored in the computer D. Also, the time interval at which a signal is received at each and every one of the receiving contact locations 36-1 through 36-n to the receiving contact point 80a and through the section 80 to the D/S C would have already been precisely measured and is also stored in the computer D.

Therefore, when the pulse is generated at 22 to travel into the transmitting point 44 and be received at the connecting point 36-1, and the total time lapse from transmitting the pulse 22 to the time when it was received at the D/S C is measured. Of course, the travel time between the transmitter 44 and the receiving point 36-1 is just zero, as the receiving location at 36-1 coincides with that of the transmitting location 44. It is possible to determine the precise time interval during which that pulse has traveled from the contact point 44 along the pipe or pipeline A and to all the receiving locations, 36-1, 36-2, . . . 36-n.

To carry this analysis further, let it be assumed that the receiving contact point 36-2 is now in operative connection to the D/S C, so that the pulse now travels through the source cable 20 to be received at the ns or fwp position 44 can be determined, and the time interval which it takes a pulse to travel that distance from 36-1 to 36-2 can also be determined. The velocity of the pulse traveling through any particular section of pipe between the adjacent receiving locations, 36-1 and 36-2, 36-2 and 36-3, etc. can also be precisely determined.

As an alternative, the difference of the electromagnetic wave propagation between two adjacent locations such as the above described, viz., the travel time and wave form differences between 36-1 and 36-2, 36-2 and 36-3, . . . 36n-1, and 36-n can be directly measured by employing a pair of directional antennas, one acting as the transmitting source antenna and the other acting as the receiving antenna. Since the transmitting and the receiving antennas are essentially identical, they can be interchanged in the profiling. They can be reversed, i.e., the source antenna acting as receiving antenna and the receiving antenna acting as the source antenna. For the ns or fwp and fs or rvp operations, the pair of transmitting and receiving antennas can be configured as a marching pair as shown in FIG. 4.

This marching pair of the source and receiving antennas have a separation between the two antennas from a few inches to several feet. Normally, the separation of the marching pair can range at least from one to five feet for a conservative resolution of detecting corrosion of about one to two feet in length.

From the description of the operation of the System as given above, it now becomes apparent that the System of the present invention is possible to determine the time interval which it takes the pulse to travel through the segment of the pipe or pipeline under test from the transmitting contact point 44 to each of the receiving contact points 36-1 through 36-n. In like manner, for a reversed profiling, it is also possible to determine the length of the time interval that it takes the pulse to travel from the transmitting contact point 51 through the pipe or pipeline A to each of the receiving contact locations in a reversed order to 36-n all the way through 36-1 (FIG. 1b).

Further, the distance between each adjacent pair of contact points 36-1 through 36-n would have been precisely measured. Thus, since the distance between each set of contact points 36-1 and 36-2, 36-2 and 36-3, etc. can be determined, and the time interval which it takes a pulse to travel that distance can also be determined, the velocity of the pulse traveling through any particular section of pipe or pipeline between the adjacent receiving locations, 36-1 and 36-2, 36-2 and 36-3, etc. can also be precisely determined to yield the information on corrosion, as the velocity for corroded pipes is slightly smaller than that for a non-corroded pipe, which will be further addressed in the sequel. The slowness is then simply 1/velocity.

Moreover, as the D/S C is interactively controlled by the computer D, the D/S C thus records not only the first arrivals at all the receiving locations, viz., 36-1, 36-2, . . . 36-n, for the ns or fwp operation, and 36-n, 36-n-1, . . . 36-1 for the fs or rvp operation that provide the travel time information for a reversed profile, but also all the wave forms or wave trains of a designated length of the record for each channel that provide additional information on the dynamic aspects of the characteristics of the electromagnetic waves, in terms of propagation, attenuation, dispersion, etc., as these waves are propagated along the pipe or pipeline under test.

Understanding of Underlying Phenomena for the Present Invention:

Dynamic Characteristics:

With the basic operation of the System having been described above, let us now discuss the underlying phenomena involved which enables this system to be effectively utilized to detect corrosion and/defects, and/or other anomalies in a pipe or pipeline A or the like. The System of the present invention uses a transient time-domain electromagnetic pulse as an excitation source and takes advantage of the fact that external corrosion on a pipeline changes the characteristics of electromagnetic wave propagation, including velocity (or its inverse, slowness), attenuation, dispersion, and phase shift. The System could be applied to detect a variety of corrosion which occur on the surface of the pipeline under insulation.

The technique utilized in the System of the present invention has been designated by the inventors as "True Electromagnetic Waves" (abbreviated to "TEMW", a trademark). The propagation of a transient electromagnetic pulse about a pipe or pipeline is fundamentally a dynamic electromagnetic phenomenon. It is completely governed by the electromagnetic wave equations, which are derived from Maxwell's Equations.

The following briefs the essential parts of the derivation, in view of the importance of these wave equations, which constitute the essence of the present invention to be applied to the detection of corrosion and/or defects of CUI.

The first two Maxwell's equations and consitutive relations for a linear and isotropic medium are:

$$\nabla \times E = -\frac{\partial B}{\partial t}, \tag{1}$$

$$\nabla \times H = \frac{\partial D}{\partial t} + J, \tag{2}$$

$$D = \varepsilon E, \tag{3}$$

$$H = \frac{1}{\mu} B, \tag{4}$$

$$J = \sigma E, \tag{5}$$

where

E=electric field in volt/m,.
H=magnetic field in A-turn/m,
D=electric displacement in $C/m^2$,
B=magnetic induction in $W/m^2$,
J=electric current in $A/m^2$,
$\epsilon$=electric permittivity in F/m,
$\mu$=magnetic permeability in H/m, and
$\sigma$=electric conductivity in mho/m.

The magnetic induction B and the electric displacement D include the externally imposed source terms $\mu$M' and P' are $$B=\mu H+\mu M', \tag{6}$$

and $$D=\epsilon E+P', \tag{7}$$

where the magnetic dipole moment density M' (A-turn/m) is related to the imposed magnetic current density $J_M$, and the electric dipole moment density P'($CM^2$) is related to the imposed electric current density Je by $$J_m = \frac{\partial M'}{\partial t}, J_e = \frac{\partial P'}{\partial t}. \tag{8}$$

By taking the curl of equation (1), introducing equation (2), and using the constitutive relations (3), (4), and (5), we obtained the electric wave field equation. The magnetic wave field equation is similarly derived.

In the Cartesian coordinate system, we thus have the electric and magnetic wave field equations, respectively as follows.

$$\left(\nabla^2 - \varepsilon\mu\frac{\partial^2}{\partial t^2} - \sigma\mu\frac{\partial}{\partial t}\right)\begin{matrix}E\\H\end{matrix} = \begin{matrix}S^e\\S^m\end{matrix}$$

Where $$S^e = \mu\frac{\partial J_e}{\partial t} + \mu\frac{\partial}{\partial t}\nabla \times M' + \nabla\frac{\rho_e}{\varepsilon} \quad (9)$$

and $$S^m = \left(\varepsilon\mu\frac{\partial}{\partial t} + \sigma\mu\right)J_m - \nabla \times J_e + \nabla\rho_m$$

are the EM sources which generate the electric and magnetic wave fields, respectively, and where Pe(C/M$^3$) and CM$^3$ (A-turn/m$^2$) are externally imposed electric and magnetic charges which presuppose that the divergence of the magnetic field is assumed not to be always vanishing.

The importance of the present invention is that we utilize the full wave field equations of (9) that opposes the traditional approaches to electromagnetics. As stated in the section b) of Background Art, the present invention is fundamentally different from those of either Spies or Lara in that Spies and Lara do not deal with the electromagnetic wave propagation, and completely neglected the term of the electromagnetic wave propagation $$\varepsilon\mu\frac{\partial^2 E}{\partial^2 S}$$

so that theirs are quasi-static dealing with a diffusion field. Inclusion of this propragating term—in the development of the present invention thus separates the PTT's techniques fgrom those of Spies and Lara, as well as others. Specifically, the present invention deals with detection of corrosion under insulation (CUI). It is based on the fact that the electromagnetic properties for good, non-corroded steel pipes are different from these for corroded steel pipes.

An electric pulse or an electromagnetic pulse may be considered as a superposition of harmonic waves. Each single frequency harmonic wave of a transient electric or electromagnetic pulse is propagated with a phase velocity, while it suffers an exponential attenuation and a phase shift. The complex propagation constant of these harmonic waves in the frequency domain thus consists of the real and imaginary parts, a and b, respectively, given by:

$$\gamma = a + ib = (-\omega^2\varepsilon\mu + i\omega\sigma\mu)^{1/2}, \quad (10)$$

where $$a = \omega(\varepsilon\mu/2)^{1/2}[(1+\sigma^2/\omega^2\varepsilon^2)^{1/2}-1]^{1/2}, \quad (b\ 11)$$

and $$b = \omega(\varepsilon\mu/2)^{1/2}[(1+\sigma^2)]^{1/2} \quad (12)$$

where the phase velocity is $\gamma = \omega/b$, and its slowness is simply $\gamma^{-1}$, and the attenuation constant a and the phase constant b.

The relative magnitude of conduction current to displacement current is given by the ratio $\sigma/\omega\varepsilon$ Of course, the degree of the effect of the conductivity $\sigma$ over the effect of permittivity $\varepsilon$ or vice versa on the electromagnetic wave propagation depends upon the frequency and the given values of the two parameters $\sigma$ and $\varepsilon$. The ratio for $\upsilon/\omega\varepsilon$ a good conductor such as steel pipes whether corroded or non-corroded is much greater than unity. However, because of corrosion, this ratio for a corroded pipe is slightly smaller than for a good pipe that is one of the physical keys to the development of the present invention.

On a corroded pipe, the corrosive material which deposits on a pipe or a pipeline thus changes both conductivity and permittivity, as well as permeability. However, the change of permeability $\mu$ in this case is relatively minor in comparison with the changes of conductivity and permittivity. The electromagnetic properties, particularly $\varepsilon$ and $\sigma$, for a good, non-corroded steel pipe are generally higher than those for a corroded pipe. Therefore, the phase velocity of the electromagnetic waves for a good, non-corroded pipe is generally higher than for a corroded pipe. And the slowness is generally lower for a good, non-corrosive pipe in comparison with that for a corroded pipe. The degree of the severity of corrosion determines the deviation of the phase velocity, or its slowness, from that for a good, non-corrosive pipe. Likewise, the attenuation of the electromagnetic waves for a corrosive pipe would be higher than that for a good, non-corrosive pipe. The phase velocity of the electromagnetic waves in a pipe, whether it is non-corrosive or corrosive are of frequency dependence so that the propagation of the electromagnetic waves in a pipe is dispersive, which introduces additional complication in dealing with waveforms The above statement of the phase velocity, attenuation, dispersion, and phase shift of the electromagnetic waves is valid for the transient electromagnetic pulse, as previously stated that a transient electromagnetic pulse always can be decomposed into Fourier components in the frequency domain.

Skin Depth

The penetration of the electromagnetic waves is controlled by skin depth, or penetration depth, which is somewhat inversely proportional to the conductivity of the medium, in which the electromagnetic waves are propagated, and the frequency of the waves. Accordingly, skin depth becomes smaller for higher frequency in good conductors, such as steel, of which pipe under question is generally made. The conductivities of the steel, HTS and HY-80, at 1 kHz and 20 C, are 4.80 and 3.50 mmho/m, respectively, and the skin depths are 0.54 and 0.90 mm, respectively (Taken from Kraichman, 1970, Handbook of Electromagnetic Propagation in Conducting Media: NAVMAT P-2302, U.S. Govt. Printing Office, Washington D.C., 20402, p.A2). In the present invention, the electromagnetic waves are propagated in the GHZ range along the steel pipe or pipeline, the skin depth for the steel pipe or pipeline would be far smaller than the above quoted numbers for steel. Therefore, the electromagnetic wave propagation about a pipeline is confined to the very surface or virtually the boundary layer of a pipe or pipeline where corrosion occurs.

Propagation Paths of Electromagnetic Waves along a Pipe:

The propagation of electromagnetic waves naturally obeys the Fermat's principle.

The first arrival and the subsequent arrivals of the electromagnetic waves about a pipe or pipeline even under insulation follow the shortest travel paths according to Fermat's principle that the first energy travels over the path which takes the least time.

The subsequent energies would travel in the shortest helicoidal paths around the pipe. Therefore, the arrivals of the electromagnetic waves would indicate the condition and degree of corrosion of the pipeline, if the travel paths encounter the corrosion and/or defects to be detailed.

The energy of the source, however, is partitioned. Likewise, there are also energies traveling in the direction away from the receiving locations along the pipe or pipeline.

Whereas electromagnetic waves reflect, refract, and diffract at the interface for example between two sections of a pipeline, i.e., a good and a corroded section, at the junction of the two different types of pipe, or simply isolated corrosion. Reflection, refraction, and diffraction of electromagnetic waves in general obey the classic laws of Snell, Fresnel, and Huygens.

Furthermore, the traveling path of the electromagnetic waves, which takes the least time depends on the positions of the transmitter and the receiving locations. If the transmitter and the receiver are located longitudinally at a distance but exactly at the same azimuthal angle, say 12 o'clock with reference to the top of the pipe, the first arrival would be a straight line. The circumferential designation of the position of the transmitter and the receiver thus here is referenced clockwisely, facing the ns or fwp position. from the direction of the fs or rvp position. Thus, the position of 6 o'clock is located on the bottom of the pipe, and the positions of 3 o'clock and 9 o'clock are located on the right-side and the left-side of the circumference of the pipe, respectively as shown in FIG. 5. The distance is measured longitudinally from the ns or fwp position toward the fs or rvp position parallel to the axis of the pipe. Therefore, if the transmitter is located at 12 o'clock and the receiver is located at the 6 o'clock at a distance 1, the path of the first arrival of the electromagnetic waves would be helicoidal. The turns of the helicoidal path depends on the mode of the electromagnetic wave propagation.

Mathematically, the helicoidal paths of the right-hand-screw and of the left-hand-screw about the pipe of a radius $\gamma_o$ can be expressed as Suppose a helix lies on a circular cylinder of radius r about the axis Z, then $$r^2 = X^2 + Y^2$$

Figure 5A:
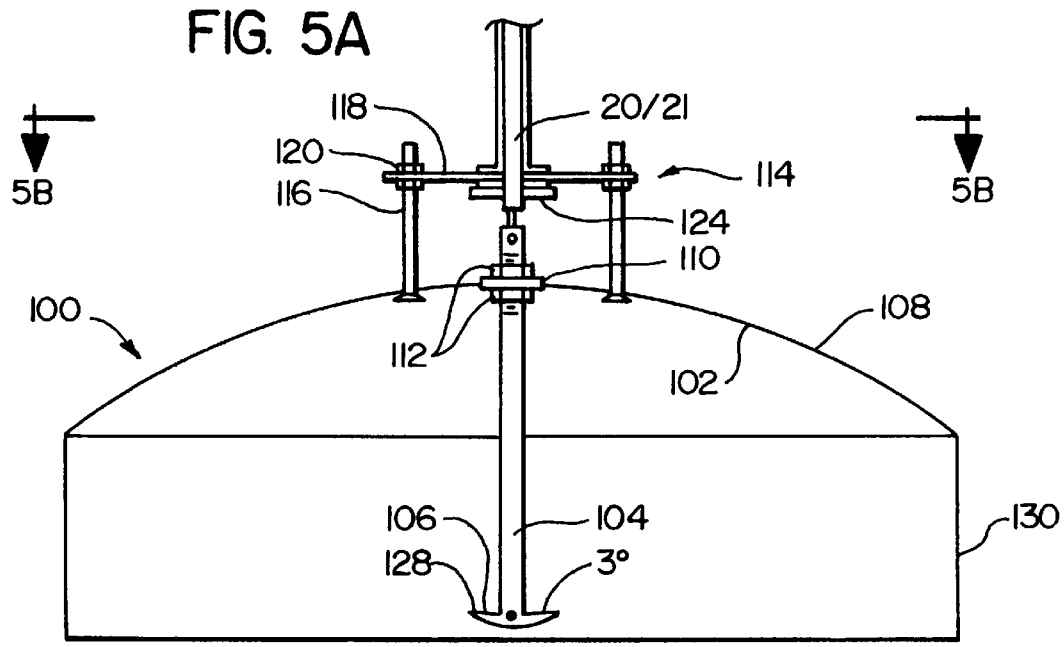
FIG. 5a is a sectional view of a transmitting and/or receiving antenna used in the present invention.
Figure 5B:
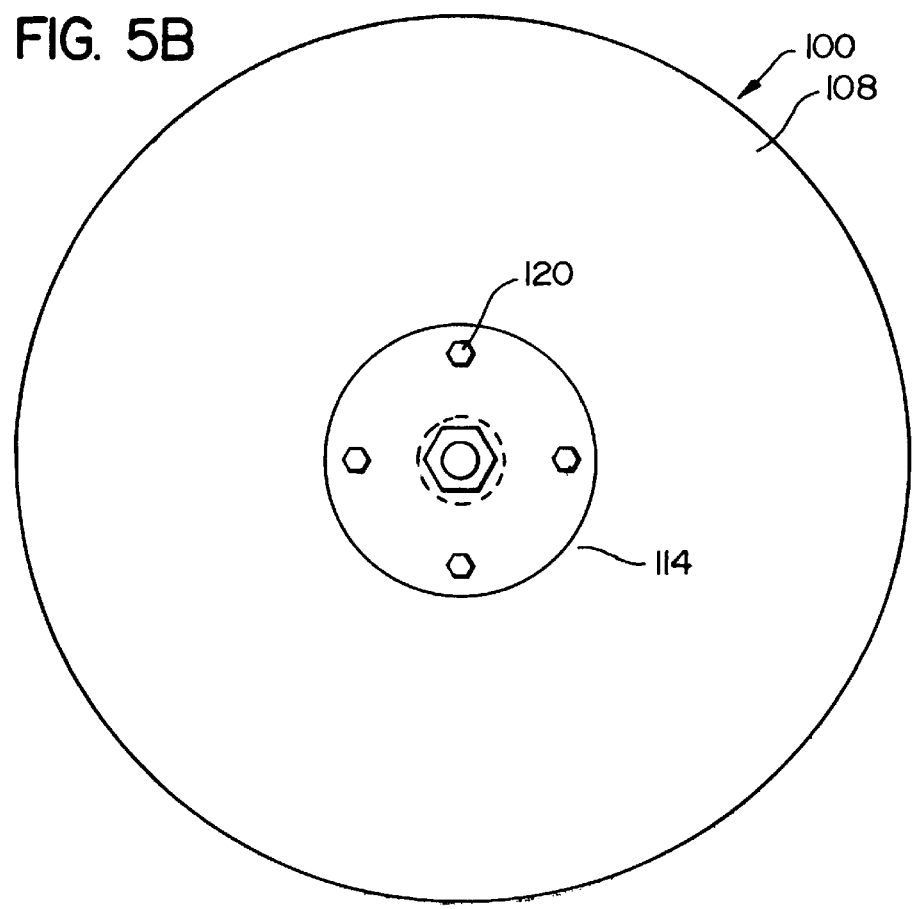
FIG. 5b is a top plan view thereof.

Suppose the distance of the successive windings at the Helix is as shown in FIG. 5A and 5B.

We choose N (r,o,o) which the helix path passes through, on the x axis and its projection on the helix path parallel to the axis will be N' (r,o,l).

Suppose A (x,y,z,) is a moving point which follows the helix path, and its projection on the x-y plane will be A' (x,y,o,). Let oA' be the line directed from o to A' . We take as positive the sense of rotation and consider that angle from the x axis to oA' whose measure O is zero when A is at N and rotates continuously as A recedes from N so that A (r cos 0, r sin 0, Z)

By the nature of the electromagnetic wave propagation, the helicoidal path would obey the Fermat's principle. Therefore, this helicoidal path would take a minimum time for the wave to travel from point N to N' on the three dimensional surface of the circular cylinder. The ratio of the velocity of the wave traveling in the direction of the helicoidal path to the velocity rotation of the cylinder about the X axis is constant.

Figure 9A:
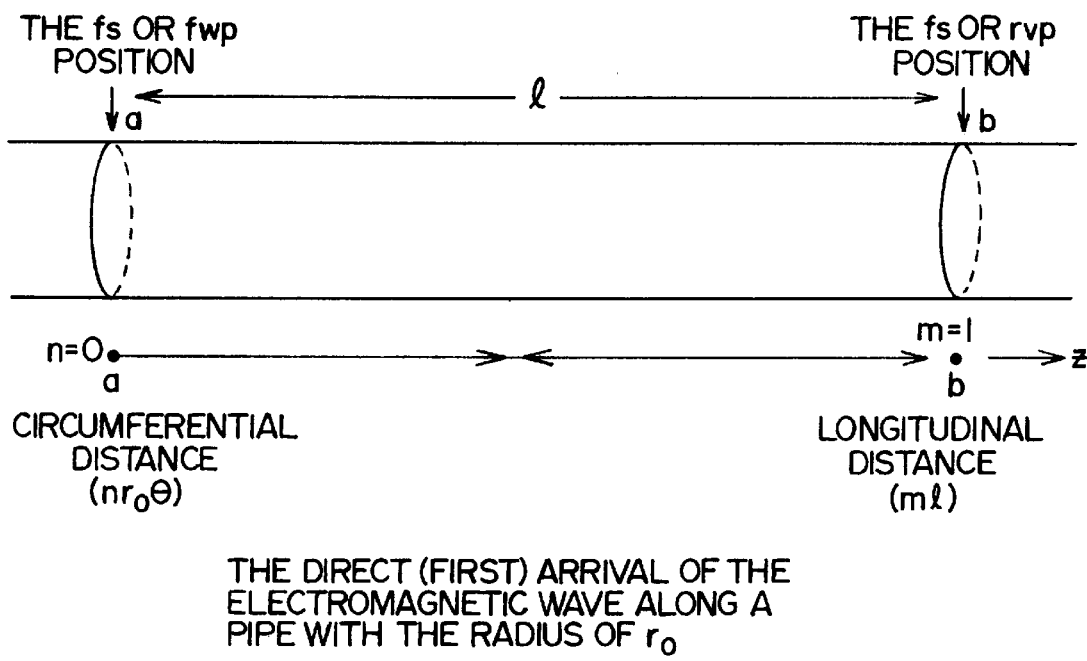
FIG. 9a is an isometric view of a pipe showing the path of a first arrival of an electromagnetic wave.
Figure 9C:
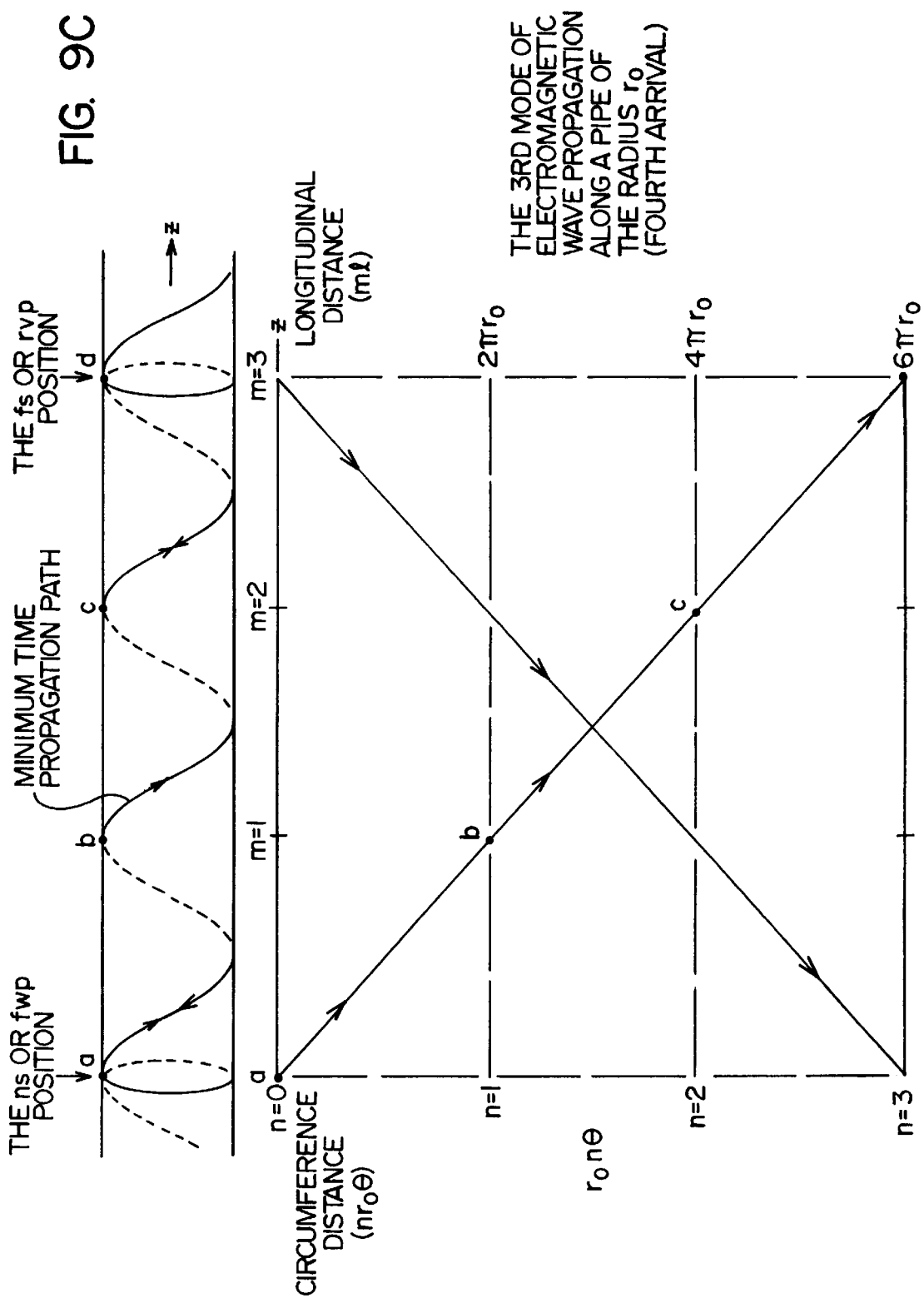
FIG. 9c is both an isometric view and plan view similar to 9b, but showing two fourth arrivals in the plan view and one fourth arrival in the isometric view.
Figure 9D:
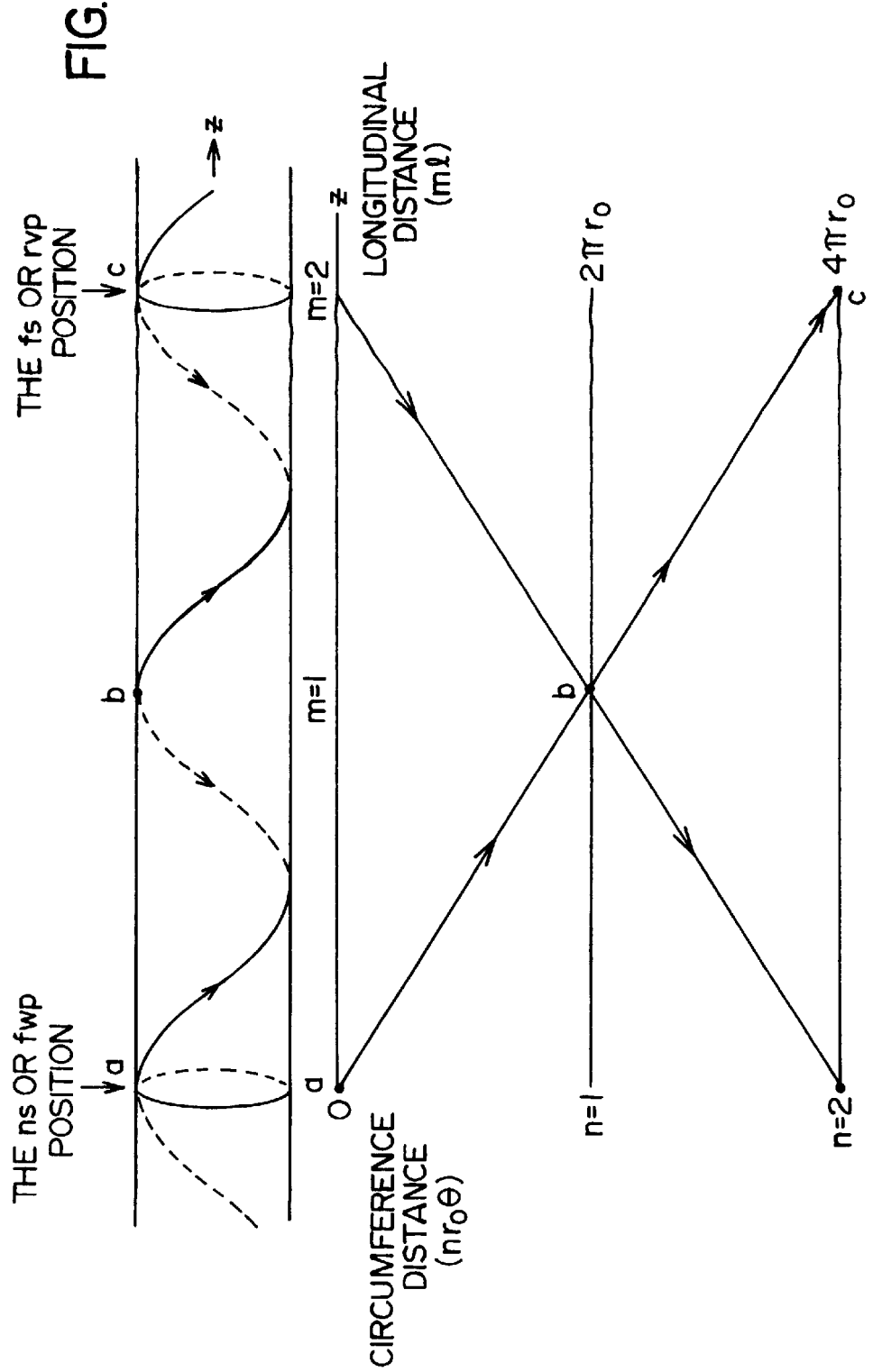
FIG. 9d is an isometric view and a two dimensional view similar to FIGS. 9b and 9c showing the paths of two second arrivals of the magnetic wave.
Figure 10A:
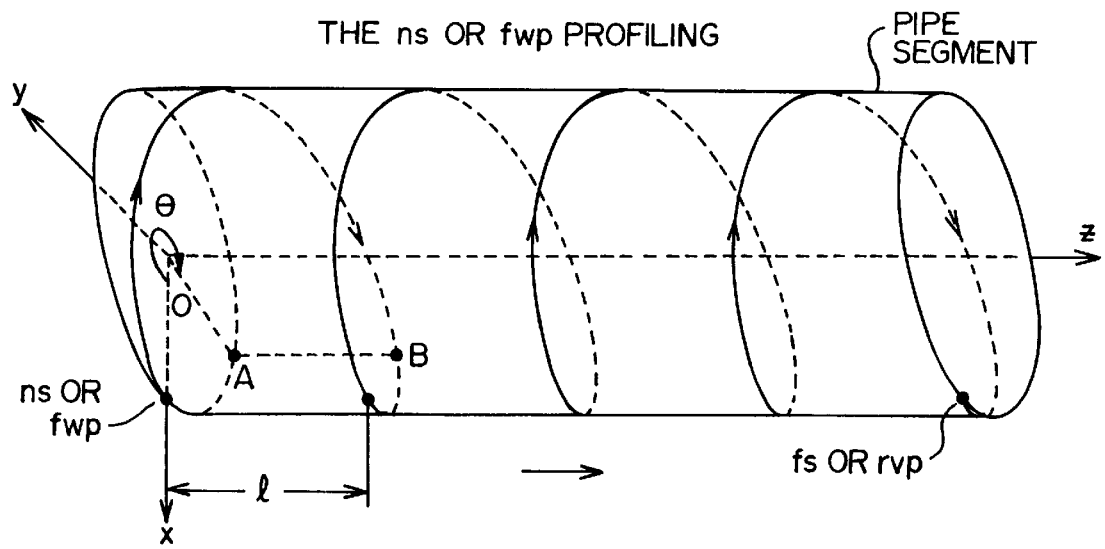
FIGS. 10a and 10 b are two isometric views showing schematically helical paths for purpose of explaining a mathematical formulas relating thereto.
Figure 10B:
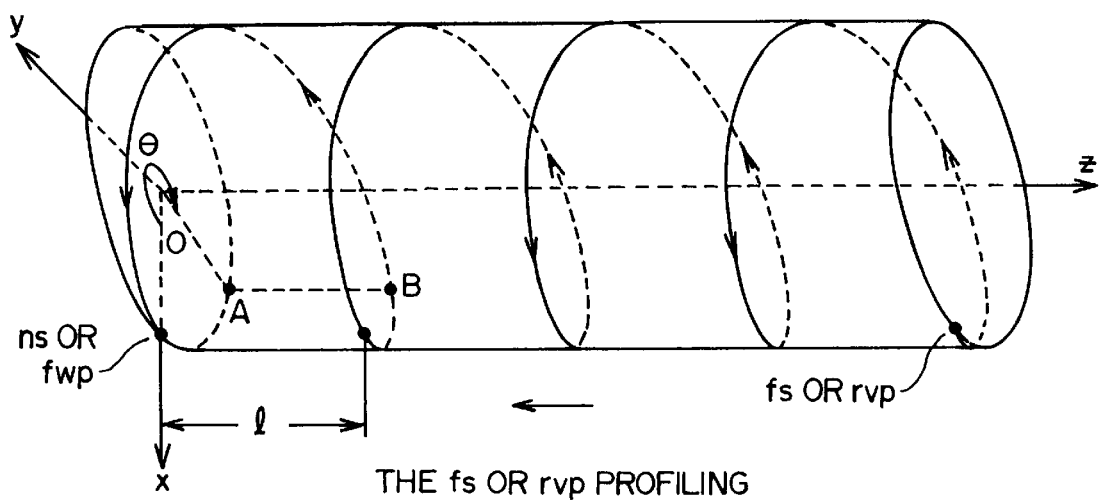

Now, we must express in terms of the change of 0. The angle that the helicoidal path makes with respect to the longitudinal line parallel to the Z axis 0, and its complimentary angle with Now, we are able to describe the helicoidal paths for the first and subsequent arrivals as shown in FIGS. 9a, b, c, and d, which illustrates not only the helicoidal paths in three dimensions but also the helicoidal paths mapped into the z-s plane in two dimensions. As expected, in two dimensions, the helicoidal paths degenerate into straight lines to represent the shortest path the electromagnetic waves travel that would take a minimum time.

From FIGS. 9a, b, c, and d, it is clear that if an isolated corrosion is located at the 12 o'clock position in the middle between the ns or fwp position and the fs or rvp potion, only the odd arrivals of the electromagnetic waves would sense the corrosion, when the transmitter and the receiver are located at the 12 o'clock position. On the other hand, if this isolated corrosion is located at the 6 o'clock position and the transmitter and the receiver remain at the 12 o'clock position, then only the even arrivals of the electromagnetic waves would sense the corrosion.

Of course, there are a number of variables which must be considered, such as the optimal positioning of the transmitter and receiver, the pulse width of the source, the location and extent of the corrosion ), etc. All these variables would play critical roles in the CUI detection. Furthermore, for illustration purposes, the propagation path of the electromagnetic waves are represented by a single ray. In actually because of the aperture of the transmitting and the receiving antennas, the propagation path of the electromagnetic waves has multi-rays, whose width are comparable to the aperture of the antennas.

Relevant Devices Developed for the Present Invention:

High-Pass Antenna Design:

Accompanying the present invention, passive source and receiving antenna have been developed.

Excitation of a pipe or pipeline by an effective source transmitter and signals received by an effective receiver are achieved by means of the developed directional antennas in the present invention.

A Passive Antenna design:

FIGS. 5a and 5b show the detailed drawing of the directional antenna 100, which comprises a parabolic reflector 102 which is made of coated plastics, metal, or metallic wire mesh, and has a width of aperture d. A prescribed optimal electric pulse from a pulse generator (See the choice of pulse width) through the source cable(s) 20, 21 becomes an electromagnetic pulse (or waves), which impinges upon the brass focus rod 104, which extends downwardly along the center axis of the parabola, and also on the focus member 106 which has a radiation-shield. The electromagnetic waves in turn are propagated and diffracted by the focus member 106 at the focus termination end into the parabolic reflector 102. The impinging electromagnetic waves from the focus rod 104 and focus member 106 are reflected from the parabolic reflector 102 to travel to the pipe A to excite the pipe A.

In order to minimize the undesired radiation from the surrounding pipes and conducting objects in a real field environment, a radiation-elimination parabolic shield 108 of the same curvature, in addition, is mounted adjacent to and coaxially with the parabolic reflector 102a. In the center of the parabolic reflector 102, there is a circular insulating disk 110, to which the threaded focus rod b is fastened by two nuts 112 on the back (convex side) and the other on the inside (concave side) of the parabolic reflector 102.

A four-posted-standoff generally designated 114 and comprising four non-conducting vertical posts 116 arranged in a square pattern, and also a mounting plate 118, is mounted on the back (convex side) of the parabolic reflector 102 by nuts 120 threaded onto the upper ends of the posts 116. Through this standoff 114 the connections between the radiation-shield and the cable, which carries the electromagnetic pulse from the initial electric pulse generated by a pulse generator propagated through the source cable 20/21 to the focus rod 104*b*. The single conducting wire of the radiation-shield coaxial cable is directly set into the focus rod 104 and securely fastened by three set screws 122, and a stabilizer 124 is mounted to the under-face of the mounting plate 118 of the four-posted-standoff 114 to prevent the mobility of the cable lead. There is a lower circumferential plexiglass skin 130 which is attached to the lower edge of the reflector 102 and extends downwardly therefrom.

On the basis of the reciprocity theorem, a passive receiving antenna is herein also used as a source transmitting antenna.

It will be noted that the upper surface 128 of the focal member 106 slants downwardly and radially inwardly toward the lower end of the rod 104. Thus there is a reflective path between the various locations on the surface of the parabolic reflector 102 to the surface 128 of the focal member 106 to the length of the brass rod 104.

The detailed design of a source antenna transmitter is the same as the above described passive antenna, except an electric pulse is generated directly from a low powered-electric pulse generation assembly. This assembly is mounted directly on the focus face of the parabolic reflector as shown in the diagram.

Used as A Passive Antenna Receiver:

An antenna receiver in the present invention is of passive type. The detailed design of a passive parabolic reflector antenna is the same as a passive antenna transmitter, except the antenna is not excited by the pulse generator but receives the electromagnetic waves as they are propagated along the pipe or pipeline and refracted (or radiated) through the insulation and the generally metallic shield of the pipe or pipeline. A simple electromagnetic ray path diagram illustrates the function of a passive receiver antenna. As the electromagnetic pulse is propagated along the pipe and refracted through the insulator and the sheet-metal shield of the pipe whether in the refineries or chemical plants, or in the actual trans-continental or interstate pipelines, the receiving antenna thus receives the electromagnetic pulse originated from the pulse generated and transmitted through the cables. These signals are attenuative, absorptive, and dispersive and subjected to radiation energy loss of the cables and the pipe or pipeline.

Circumference Distributed Source and Receiving Antennas:

For a large-diameter pipe, corrosion of the pipe or pipeline are generally not distributed about the circumference throughout, a circumference-distributed transmitting antenna of Type A (see FIG. 6*a*) using three antennas distributed at 120 deg apart, and of Type B (see FIG. 6*b*) using six antennas distributed at 60 deg. apart about the circumference in the form of a ring are being developed as shown in the diagram. Sources S1, S2 and S3 for Type A and sources S1, S2, . . . S6 of type B as designated can be excited simultaneously or one at a time as desired by means of an electric-pulse generator through the source cable and controlled by a multi-connecting switch and controlled by a computer as shown in FIG. 8.

Likewise, circumference-distributed receiving antenna assumes the same geometrical configuration, as the circumference-distributed source antenna. Signals from the individual receiving antenna of the circumference-distributed antenna can be recorded by any elemental antenna individually, all the elemental antennas simultaneously, or any combination of the elemental antennas controlled by a multi-connecting switch and a computer.

Choice of Optimal Pulse-Width:

The choice of an optimal pulse width is of importance in detection of corrosion in a pipe or pipeline. For detection of corrosion, a fast-rise and narrow pulse width (one nanosecond or less), or a wide-open square wave with a pulse width greater than 1us (one microsecond) or even 1 ms (one millisecond), is preferred, depending on the separation of the transmitter and receivers. A wide-open square wave simulates Heaviside step functions, while a very narrow pulse approximately simulates a delta function. However, for a wide-open pulse, the two responses from a positive Heaviside—and a negative Heaviside step functions must not be overlapped and interfered in data acquisition. For the present invention, a preferred pulse width is 1 ns or less with a repetition-rate of about than 1 to 10 kHz.

Wide-open Square Wave:

A pulse width of $\mu$s or 1 ms square wave provides a positive Heaviside step or a negative Heaviside step function. The response of the cable to a Heaviside step function is essentially a RC-type decayed step function, the arrival of which is very difficult to be accurately determined. When the step function impinges on a pipe, the pipe excites high frequency components, which are comparatively more attenuative and dispersive than the step function pulse which is propagated in the co-axial cable The response of the cable(s) to the electric pulse excitation must be removed from the total response in order to analyze the response of the pipe to the propagation of electromagnetic waves.

One of the convenient methods for removing the response of the cable(s) from the response of the cable(s) and the pipe or pipeline is by means of a high-pass receiving antenna, which is to be co-patented in the present invention.

Narrow Pulse-width Pulse:

For detailed detection of corrosion, it is desirable that the pulse width be made as narrow as possible with its minimum of 1–2 ns and preferably in the picasecond range so that the first arrival and the subsequent arrivals would be separable.

With the present state-of-the-art, the stability of a pulse generator to generating such an extremely narrow pulse of much less than 1 ns is a challenge. Nevertheless, a pulse of 1 ns (i.e. one nanosecond) is quite attainable that would have a wavelength of about 1 foot. The resolution of detecting corrosion with a 1 ns pulse would be in the neighborhood of 1–2 feet. An extremely narrow pulse, if its center-frequency is in the neighborhood of 10 GHz and a pulse width of 100 ps would be ideal. It then would have a wavelength of about 1 inch in a steel pipe or pipeline.

Sweeping Excitation Function:

For determination of the precise arrival time of the electromagnetic waves, in addition to a wide open square wave and the fast-rise very narrow pulse, a chirping sweep of excitation source can also be used.

Since the electromagnetic waves propagated along the pipe or pipeline are either inversely dispersed or normal dispersed, a high-to-low sweeping and a low-to-high sweep of excitation source in the frequency of a gigahertz range can be used, respectively. The data processing of the sweeping source functions thus can be implemented by moving window cross correlation technique.

Positioning Transmitter and Receiver:

Detection of corrosion in a pipe or pipeline in question particularly of large diameters must optimally position the transmitter and receiver for either the single-pulse or the dual-pulse techniques using a single cable or multi-channel cable. Proper positioning the transmitter and receivers thus allows the wave propagation paths to cover certain cross section(s) in circumference-wise and certain portion of the pipe or pipeline in length-wise.

In the cross section along the circumference, the transmitter and the receiver can be aligned in the same azimuthal angle or the longitudinal direction. Likewise, the transmitter can be positioned at the 12 o'clock position, and the receiver be positioned at any o'clock position, say 3, 6, 8, 9 . . . 11 o'clock position. Vice versa, while the receiver is positioned at one particular position, the transmitter is positioned at various positions along the circumference of the pipe or pipeline. Although there are many exceptions, corrosion generally occurs near the bottom of a horizontal pipe or pipeline, i.e., about the 6 o'clock position, where the moisture condensates and water accumulates most.

The above method of positioning the transmitter and the receiver thus leads to the development of the circumference-distributed transmitter and the circumference-distributed receiver by means of a relay switch to be pre-programmed and controlled by a computer to transmit the electromagnetic pulse from a transmitter at a designated position to be received at any azimuthal angle as desired or any other combination of positioning the transmitter(s) and the receiver(s).

Corrosion under insulation (CUI)

a. Corrosion in a Relatively Small Diameter Pipe:

With the foregoing in mind, let us now turn our attention back to FIGS. 1*a* and 1*b*, 2*a* and 2*b*, and 3*a* and 3*b*, and assume that there is a corroded section E on the steel pipeline A and that this extends from a location from the contact point 36-4 beyond the contact point at 36-5 and part way to the contact point 36-6. Let us further assume that the remainder of the pipe A on both sides of this corrosion area E have no corrosion so that the segment of the pipe or pipeline A at these other sections would be uniform.

Let us assume that the test procedure has been utilized as described above, namely that it begins by transmitting pulses from the cable end 22 and into transmitting contact point 44, where the transmitter is located, and that these pulses are received by the various channels in sequence or multiplexed, first at the receiving location 36-1, received at the receiving location 36-2, all the way to the last receiving location 36-N$_y$.

As described previously herein, with all of the time interval characteristics of all the components of the System having been already predetermined, it is possible to ascertain the travel time during which a pulse travels, for example, from the transmitting contact point 44, which is also the first receiving contact point 36-1, from the transmitting contact point 44 to the receiving contact point 36-2, etc. Thus, (also as described previously herein), it is possible to calculate the time interval between which a pulse would travel between any two points, i.e., between the point 44 and any one of the points 36-1 through 36-n, also in reverse from the transmitting contact point 51 to any one of the receiving contact points 36-n through 36-1.

Thus, when the pipe or pipeline A, as shown in FIGS. 1*a* and 1*b*, is being tested, and the data are analyzed so that the distance between the source transmitting point 44 and each of the receiving contact points plotted along a horizontal axis, and the travel time for the source transmitting point to each of the receiving contact points is plotted along the vertical axis, for those portions of the pipe under test which have not been subject to corrosion, the related portions of the curve would have a constant slope to indicate a given velocity which is characteristic of the uncorroded sections of the pipe A. However, the portions of the curve relating to the sections of the pipe which have been corroded would have a steeper slope, thus indicating a reduction of velocity at these locations.

Also, as indicated previously, since the time interval for a pulse to travel between any of these two points 36 can be determined and the distance between these contact points 36 on the pipe A has already been measured, it is possible to measure the velocity of the wave propagated between any two pair of contact points 36. The data thus yield the differences of the travel time between a pair of the adjacent receiving contact points, 36.

Reference is now made to FIG. 7 which is a simplified graph which shows how the curves might appear when the pipe section shown in FIG. 1*a* and 1*b* is being tested, and with the corrosion area E being positioned as shown in FIGS. 1*a* and 1*b*, 2*a* and 2*b*, and 3*a* and 3*b*. It is apparent from the discussion presented above that where the corrosion zone E extends the full length from the contact point at 36-4 and 36-5 that the velocity of the pulse traveling between point 36-4 and 36-5 would become slower. Part of the pipe section between the contact points 36-5 and 36-6 is also in the corrosion area 6, and (depending upon various factors) it may well be that the pulse in traveling along the pipe section from the contact point 36-5 to 36-6 would have the phase velocity reduced, but not quite as much as in the test section between 36-4 to 36-5.

To relate this to the graph shown in FIG. 7, the curve portion at 62 represents the time and distance values of the pulses traveling through the pipe test section from the contact locations 36-1 through 36-4. Since the pipe section between the points 36-1 and 36-4 is uniform, the slope at 62 would be uniform. At the pipe section between points 36-4 to 36-5 the corresponding portion 64 of the curve is at a steeper slope, indicating that the velocity is decreased. Then the pulse in traveling from the contact location 36-5 and 36-6 would experience a velocity less than the pulse traveling through the pipe section from 36-1 to 36-4, but possibly somewhat faster than the pulse traveling through the pipe section from contact point 36-4 to 36-5. From the contact location 36-6 on to the end of the test section at 36-n, the curve portion 68 would have substantially the same slope as the curve at 62, since the pipe section from 36-6 to 36-n is non-corroded, and thus again has a uniform cross section.

Then when the second part of the analytical testing process is done, the curve starts at the contact location 36-n and continues upwardly toward the left. Since the pipe section from contact point 36-n to 36-6 is not corroded, the curve portion 70 corresponding to this pipe section has substantially the same slope as the curve portions at 62 and 68. At the curve portions indicated at 72 and 74, it will be observed that the slope of these two portions are, respectively, the same as the curve portions 66 and 64. Then, the curve portion 76 corresponding to the path of travel from the contact point 36-4 to 36-1 has the same slope as the curve portion at 70. Thus, the two curves are substantially mirror images of one another. One of the important points is that by virtue of reciprocity the amount of travel time from A to B and from B to A in principle, must be the same, (i.e. $T_A = T_B$) at least for the first arrival. However, under an asymmetrical case of corrosion configuration that principle of reciprocity may not hold, i.e., the traveling paths for a given mode for the ns or fwp and fs or rvp profiling may be slightly different.

By testing the pipe section in both directions, verification is given to the readings. Beyond this, however, there may be additional benefits in measuring the propagation of the pulses in both directions. For example, it is possible that depending upon the particular pattern of corrosion, for late arrivals there could be differences in the manner of wave propagation.

An Isolated Corrosion on a Large-Diameter Pipe:

Detection of a small isolated corrosion in a large-diameter pipe requires further consideration. In principle if the isolated corrosion is located in the propagation path of the electromagnetic waves, these waves would pass through the isolated corroded portion of the pipe. Nevertheless, the electromagnetic waves always seek to take the shortest path which would take a minimum amount of time. If the electromagnetic waves would take a longer time to propagate across the spot of the isolated corrosion then the waves take a detoured diffracted path around the small corrosion, the waves would take the latter diffracted path, which is comparatively a shorter path with a least time..

Because the waves take a detoured diffracted path around the small isolated corrosion, it also results in a time delay, which is not directly related to the time delay for the waves passing through the corroded portion of the pipe, but it is indirectly related to the presence of the isolated corrosion. Although it will be difficult to differentiate the two different time delays, the actual time delay would still be an indicative of the presence of a small, isolated corrosion.

Attenuation, Dispersion, and Phase Shift:

In addition to the changes in velocity of the pulse traveling through the corrosion area, it is surmised, based upon analysis and experimental results, that valuable information can be obtained from analyzing the waveforms themselves. Thus, the signal analyzer C would form what might be termed "electromagnetograms" for the wave forms (which the originators have abbreviated to "EMGRAMS"), from which travel time, attenuation, dispersion and phase shift of the electromagnetic signal are analyzed. This process of field measurements has (as indicated previously herein) been termed by the inventors as "True Electromagnetic Waves" (abbreviated to "TEMW").

The result of the forward-and reverse-profiling would include TT-X (travel time in nanoseconds versus distance in feet, the slope of which gives slowness and its inverse, velocity), V-X (voltage versus distance, the graph of which yields attenuation of the electromagnetic wave propagation), U W (group velocity versus frequency at each electric contact point with the pipeline that would give the dispersion characteristics), and the O W (phase shift versus frequency, which gives the phase shift).

The signal analyzer C could be, for example, a DSA 601 or 744 signal analyzer made by Tektronics (which in the vernacular could be termed a "smart oscilloscope"). Also, as further analysis is done, this signal analyzer could be a combination of instruments, including a spectrum analyzer similar to a family of analyzers. This could measure time, attenuation, dispersion, phase shift, and frequency content through special processing software on computers.

The pulse generator B could be a pulse generator similar to the Stanford Research System generator DG 535A, this having a 200 picasecond jitter. The interactive computer D could be a high speed PC personal computer or work stations, such as currently available (Pentium-chip computers). This computer would control the various functions described herein, collect and store the data, and with an additional computer perform demultiplexing, stacking, display, and manipulating data for data processing and interpretation.

Tests incorporating the system of the present invention have been performed on steel pipes of four inch diameter and also twenty-four inch diameter. The width of the pulses imposed on the pipe have been as great as one millisecond, and could also be less than one nanosecond. The pulses used have been square waves. The voltage of the pulses could vary, and these could be as high as four volts or higher, or as low as possibly one hundred millivolts or lower, either plus or minus voltage, with current few milliamps so that the power is less than one watt.

It is to be recognized that various modifications could be made in the present invention without departing from the basic teachings thereof.

What is claimed is:

1. A method of identifying corrosion on an electromagnetically permeable elongate member, such as a pipe, said method comprising:
   a. transmitting an electrical or electromagnetic pulse into said elongate member at a transmitting location of the elongate member and at a transmitting time, to cause said pulse to travel as a propagating electromagnetic wave to a receiving location over a travel distance and during a travel time interval;
   b. receiving at a receiving time said electromagnetic wave at said receiving location on said elongate member;
   c. ascertaining a delay in said electromagnetic wave traveling over said travel distance to ascertain presence of corrosion on said elongate member.

2. The method as recited in claim 1, wherein said pulse wave or waves has a sufficiently high frequency, so that the electromagnetic wave travels over the outside surface of the elongate member at a very thin skin depth where corrosion on an exterior surface of the elongate member may be present.

3. The method as recited in claim 1, wherein a receiving means is operatively positioned at said receiving location to receive said electromagnetic wave, and said receiving means comprises an antenna responsive to electromagnetic radiation.

4. The method as recited in claim 1, wherein said receiving means comprises a plurality of receivers which are operatively positioned at spaced receiving locations along a lengthwise axis of said elongate member, said method further comprising:
   a. ascertaining distances between said spaced receiving locations;
   b. ascertaining times of travel of said electromagnetic wave between said receiving locations;
   c. ascertaining, from said distances and said times of travel, velocity of said electromagnetic wave or waves between said receiving locations to identify presence of corrosion.

5. The method as recited in claim 4, said method further comprising ascertaining an area or areas between two receiving locations where the velocity of the electromagnetic wave or waves is lower, to identify presence and location of corrosion.

6. The method as recited in claim 5, wherein there is provided a multi-channel cable, comprising a plurality of channels, and each of said receivers is operatively connected to a related one of said channels, with said multi-channel cable directing signals received from said receivers to a data receiving location.

7. The method as recited in claim 6, wherein said multi-channel cable is a fibre optic multi-channel cable.

8. The method as received in claim 6, wherein said multi-channel cable is an electrically conductive multi-channel cable.

9. The method as recited in claim 6, wherein said pulse is transmitted to said elongate member by directing a pulse from a pulse generator to a transmitter at said transmitting location, with the transmitter in turn transmitting an electric or electromagnetic pulse into the elongate member at the transmitting location, and said multi-channel cable transmits the received signals to a data acquisition/signal analyzer means.

10. The method as recited in claim 9, wherein said pulse generator transmits a triggering signal to a data acquisitions/signal analyzer.

11. The method as recited in claim 10, wherein said pulse is transmitted into a first end of a section of the elongate member which is under test, and is received at a second end location of said section of the elongate member for forward profiling of said section, said method further comprising transmitting a second pulse or set of pulses from the second end of the section of the elongate member under test for reverse profiling toward the first end of the section of the elongate member, where the signal is received and delivered to a data receiving location.

12. The method as recited in claim 1, wherein a transmitter is positioned at said transmitting location to transmit the pulse into the elongate member, and a receiver is positioned sequentially at a plurality of spaced receiving locations along said elongate member, and pulses are transmitted into said elongate member for each receiving location at which the receiver is placed, and signals received by the receiver at the receiving locations are transmitted to a data receiving location.

13. The method as recited in claim 1, wherein said elongate member is a pipe having an insulating layer, said method further comprising providing a receiver which is an antenna responsive to electromagnetic radiation, and said receiver is placed adjacent to an outer surface of the insulating layer of the pipe to receive the electromagnetic wave.

14. The method as recited in claim 13, wherein there is a transmitter to transmit the pulse into the pipe, and a portion of the insulation is removed at the transmitting location, and the transmitter is placed adjacent to the pipe at the transmitting location.

15. The method as recited in claim 14, wherein the transmitter comprises an electrical contact member which is placed into direct contact with the pipe, and an electric current is transmitted to the transmitter.

16. The method as recited in claim 14, wherein the transmitter is a directional antenna, which is positioned adjacent to the pipe, and an electric pulse is transmitted to the antenna, which in turn transmits an electromagnetic pulse into the pipe.

17. The method as recited in claim 14, wherein there is a receiving means positioned adjacent to said pipe, said receiving means comprising a plurality of antennas which are placed adjacent to the insulation of the pipe at a plurality of receiving locations.

18. The method as recited in claim 1, wherein there is provided at the transmitting location a plurality of transmitters which are spaced circumferentially from one another, and a plurality of electric or electromagnetic pulses are transmitted from said transmitters into said elongate member, either sequentially, simultaneously, or both simultaneously and sequentially toward a receiving location or locations.

19. The method as recited in claim 18, wherein there is a plurality of receivers at the receiving location, which are spaced circumferentially from one another, said method further comprising transmitting pulses as electromagnetic waves from selected transmitters at said transmitting location to the receives at said receiving location in selected patterns.

20. The method as recited in claim 1, wherein there is a plurality of receivers at said receiving location, said method further comprising transmitting a pulse toward said receiving location, and one of said receivers, or a plurality of said receivers is operated to receive the electromagnetic wave generated by the pulse and transmit a received signal to a data collecting location.

21. A system for identifying corrosion on an electromagnetically permeable elongate member, such as a pipe, said system comprising:
 a. a transmitter means to transmit an electric or electromagnetic pulse wave(s) into said elongate member at a transmitting location of the elongate member and at a transmitting time, to cause said pulse to travel as a propagating electromagnetic wave to a receiving location over a travel distance and during a travel time interval;
 b. a receiving means to receive said electromagnetic wave at said receiving location on said elongate member;
 c. means to ascertain a time interval of travel of said electromagnetic pulse or wave(s) from said transmitting location to said receiving location
 whereby a delay in said electromagnetic wave traveling over said travel distance can ascertain presence of corrosion on said elongate member.

22. The system as recited in claim 21, wherein said transmitter is characterized in that it transmits a pulse that has a sufficiently high frequency, so that the electromagnetic wave travels over the outside surface of the elongate member at a very thin skin depth where corrosion on an exterior surface of the elongate member may be present.

23. The system as recited in claim 22, wherein said receiving means comprises an antenna responsive to electromagnetic radiation.

24. The system as recited in claim 21, wherein said receiving means comprises a plurality of receivers which are operatively positioned at spaced receiving locations along a lengthwise axis of said elongate member, said system further comprising means to ascertain intervals of time of travel of said electromagnetic wave between said transmitting locations and said receiving locations.

25. A system as recited in claim 24, said system further comprising means to ascertain intervals of travel time between various pairs of receivers to identify where the velocity of the electromagnetic wave or waves is lower, to identify presence and location of corrosion.

26. The system as recited in claim 25, wherein there is a multi-channel cable, comprising a plurality of channels, and each of said receivers is operatively connected to a related one of said channels, with said multi-channel having an operative connection to a data receiver to direct signals received from said receivers to the data receiver.

27. The system as recited in claim 26, wherein said multi-channel cable is a fibre optic multi-channel cable.

28. The system as recited in claim 26, wherein said multi-channel cable is an electrically conductive multi-channel cable.

29. The system as recited in claim 26, wherein there is a pulse generator to transmit the pulse to the transmitter at said transmitting location, with the transmitter in turn transmitting an electric or electromagnetic pulse or wave(s) into the elongate member at the transmitting location, and a data acquisition/signal analyzer means connected to said multi-channel cable to receive signals from the multi-channel cable.

30. The system as recited in claim 29, wherein said pulse generator transmits a trigger signal to the data acquisition/signal analyzer means.

31. The system as recited in claim 30, wherein there is a first transmitter at a first end of a section of the elongate member which is under test, and a first receiver at a second end location of said section of the elongate member for forward profiling of said section, said system further comprising a second transmitter at the second end location to transmit a second pulse or set of pulses from the second end of the section of the elongate member under test for reverse profiling toward the first end of the section of the elongate member, a second receiver to receive the electromagnetic wave at a second receiving location at the first end of the section.

32. The system as recited in claim 21, wherein the receiving means is a portable receiver adapted to be positioned sequentially at a plurality of spaced receiving locations along said elongate member, whereby pulses are transmitted into said elongate member for each receiving location at which the portable receiver is placed, a data receiver operatively connected to the portable receiver in a manner to permit the receiver to be moved to the receiving locations.

33. The system as recited in claim 21, wherein the transmitter comprises an electrical contact member which is placed into direct contact with the pipe, and an electric pulse is transmitted to the transmitter.

34. The system as recited in claim 21, wherein the transmitter is a directional antenna, which is positioned adjacent to the elongate member and an electric pulse is transmitted to the antenna, which in turn transmits an electromagnetic pulse or waves (S) into the elongate member.

35. The system as recited in claim 21, wherein said elongate member is a pipe having a layer of insulation, and said receiving means is positioned adjacent to said pipe, said receiving means comprising a plurality of antennas which are placed adjacent to the insulation of the pipe at a plurality of receiving locations.

36. The system as recited in claims 35, wherein the transmitter is a directional antenna, which is positioned adjacent to the pipe, whereby an electric pulse can be transmitted to the antenna, which in turn transmits an electromagnetic pulse into the pipe.

37. The method as recited in claim 35, wherein said transmitter means comprises a plurality of transmitters which are arranged in a pattern spaced circumferentially from one another, whereby a plurality of electric or electromagnetic pulses or wave(s) can be transmitted from said transmitters into said elongate member, either sequentially, simultaneously, or both simultaneously and sequentially toward a receiving location or locations.

38. The system as recited in claim 37, wherein said receiving means comprises a plurality of receivers which are arranged to be spaced circumferentially from one another, whereby pulses can be transmitted from selected transmitters at said transmitting location to said receivers in selected patterns.

39. The system s recited in claim 21, wherein said receiving means comprises a plurality of receivers spaced circumferentially from one another.

40. The method as recited in claim 1, wherein two pulses are transmitted into said elongate member in timed relationship to travel as waves toward one another to intersect at an intersecting location on said elongate member, said method further comprising receiving said intersecting waves with a receiver at a receiving location which is at said intersecting location or proximate to said intersecting location, for identification of corrosion and/or location of corrosion.

41. The method as recited in claim 40, further comprising coordinating timing of transmission of said pulses and said receiving location in a manner that said receiving location and said intersecting location coincide.

42. The method as recited in claim 41, wherein timing of said two pulses is adjusted to match the intersecting location with the receiving location where the receiving location is known, as a means of ascertaining location of the intersecting location.

43. The method as recited in claim 40, where a plurality of pairs said two pulses are transmitted in varying timed relationship so that each of some of said pairs of pulses intersect at a plurality of differing intersecting locations, and the timing of the pulses of said plurality are coordinated with a plurality of receiving locations so that intersecting waves are received to identify corrosion and/or location of corrosion.

44. The method as recited in claim 43, wherein timing of the transmission of the pulses is adjusted to cause said intersecting locations to be coordinated with said receiving locations.

45. The method as recited in claim 43, wherein wave forms received from intersecting waves by a receiver or receivers at said receiving locations are analyzed to identify corrosion.

46. The method as recited in claim 1, wherein there is a plurality of receivers at the receiving location, which are spaced circumferentially from one another, said method further comprising receiving transmitted pulses at one or more of said receivers of said plurality.

47. The method as recited in claim 1, further comprising transmitting said pulse at a first circumferential location on said elongate member to a receiving location which is spaced circumferentially on said elongate member from the circumferential location at which the pulse was transmitted into the elongate member.

48. The method as recited in claim 1, wherein the pulse transmitted into said elongate member travels as a wave form having earlier and later arrivals at said receiving location so that the wave form that arrives at the receiving location comprises a plurality of wave form arrivals said method further comprising analyzing the wave form received at the receiving location relative to phase shift, dispersion, or continuation, and/or a combination of two or more of phase shift, dispersion and continuation.

49. The method as recited in claim 1, wherein said pulse is transmitted from a pulse generator to travel to said transmitting location of the elongate member, and said pulse is received at the receiving location which is at or closely adjacent to said transmitting location and timing of the arrival at the receiving location is utilizing in ascertaining time of travel of other pulses as waves to other receiving location in said elongate member.

50. The method as recited in claim 1, wherein said pulse is transmitted into said elongate member by means of a transmitter, and said transmitter is also used as a receiver to receive a pulse in the form of a wave transmitted into said elongate member from a transmitting location spaced from said transmitter.

51. The method as recited in claim 1, wherein there is provided a reference elongate member having properties similar to said elongate member on which corrosion is to be identified, and a pulse or pulses are transmitted into said reference elongate member and received from elongate member, with ascertainment of travel time relative to distance on said reference elongate member to provide a reference against which comparable travel time in the elongate member that is being tested for corrosion can be compared.

52. The method as recited in claim 1, wherein said elongate member is a pipe having a layer of insulation said pipe, and an antenna is positioned outside of said insulating layer to receive the wave.

53. The method as recited in claim 52, where there is also a metallic shield surrounding said layer of insulation, and said antenna to receive the wave is positioned outside of said metallic shield.

54. The method as recited in claim 1, wherein a cable or cables are utilized to transmit and/or receive pulses and/or receive pulses, and said cable or cables radiation of shielded cables.

55. The method as recited in claim 54, wherein said pulse is transmitted as an electrical pulse through a radiation shielded cable to the transmitting location, and the electromagnetic wave received at the receiving location is transmitted through a radiation shielded cable.

56. The method as recited in claim 1, wherein said pulse that is transmitted to said transmitting location is a square wave pulse.

57. The method as recited in claim 1, wherein the pulse transmitted into the elongate member has a length that is between one nanosecond and one millisecond.

58. The method as recited in claim 1, wherein said pulse is transmitted to elongate member has a pulse length which is less than one nanosecond.

59. The method as recited in claim 1, wherein the pulse that is transmitted to the elongated member has a pulse length greater than one millisecond.

60. The method as recited in claim 1, wherein said pulse has a voltage between about 100 millivolts and 4 volts.

61. The method as recited in claim 1, wherein the voltage of the pulse that is transmitted to the elongate member has a voltage of 4 volts or greater.

62. The method as recited in claim 1, wherein voltage of the pulse transmitted to the elongate member has a voltage level of 100 millivolts or less.

63. The method as recited in claim 1, wherein there is a transmitter to transmit the pulse and a receiver to receive the pulse and said transmitter and receiver are moved sequentially along the elongate member to differing transmission transmitting and receiving locations so as to ascertain corrosion at differing locations at said elongate member.

64. The method as recited in claim 63, wherein said transmitter is an antenna and said receiver is an antenna, and said transmitting and receiving antennas are moved along said elongate member to ascertain corrosion at different segments of said elongate member.

65. The method as recited in claim 1, wherein said wave is received by a receiving antenna which is a high pass receiving antenna.

66. The method as recited in claim 1, wherein said elongate member is a pipe, and the pulse transmitted into the pipe travels a shortest route to the receiving location, and also the wave travels along a plurality of heliocoidal paths along said pipe to said receiving location, where one or more of said heliocoidal said paths passes through an area of corrosion, and one or more others of said paths does not pass through said area of corrosion, whereby there are earlier and later arrivals of the wave form, some of which are more affected by the corrosion than others, said method comprising analyzing said wave form to detect deviations from a reference wave form, which deviations result from modifications of wave form components traveling on different heliocoidal paths.

67. The method as recited in claim 6 where in said multichannel cable has first and second ends, both of which are attached to a receiving apparatus, said method further comprising transmitting pulses in a first direction along said elongate member for forward profiling of said elongate member and transmitting pulses in an opposite direction for reverse profiling of said elongate member.

* * * * *